(12) United States Patent
Hlavka et al.

(10) Patent No.: US 6,619,291 B2
(45) Date of Patent: Sep. 16, 2003

(54) METHOD AND APPARATUS FOR CATHETER-BASED ANNULOPLASTY

(76) Inventors: Edwin J. Hlavka, 40 Kent Pl., Palo Alto, CA (US) 94301; Paul A. Spence, 5818 Orion Rd., Louisville, KY (US) 40222

(*) Notice: Subject to any disclaimer, the term of this patent is extended or adjusted under 35 U.S.C. 154(b) by 0 days.

(21) Appl. No.: 09/841,968

(22) Filed: Apr. 24, 2001

(65) Prior Publication Data

US 2002/0156526 A1 Oct. 24, 2002

(51) Int. Cl.⁷ .............................................. A61B 19/00
(52) U.S. Cl. ....................... 128/898; 623/904
(58) Field of Search .............................. 623/2.38–2.41, 623/2.11, 904; 128/898; 606/151

(56) References Cited

U.S. PATENT DOCUMENTS

| | | | |
|---|---|---|---|
| 4,042,979 A | 8/1977 | Angell | 3/1.5 |
| 4,055,861 A | 11/1977 | Carpentier et al. | 3/1.5 |
| 4,489,446 A | 12/1984 | Reed | 3/1.5 |
| 4,917,698 A | 4/1990 | Carpentier et al. | 623/2 |
| 5,041,130 A | 8/1991 | Cosgrove et al. | 623/2 |
| 5,061,277 A | 10/1991 | Carpentier et al. | 623/2 |
| 5,104,407 A | 4/1992 | Lam et al. | 623/2 |
| 5,201,880 A | 4/1993 | Wright et al. | 623/2 |
| 5,306,234 A | 4/1994 | Johnson | 604/49 |
| 5,306,296 A | 4/1994 | Wright et al. | 623/2 |
| 5,360,444 A | 11/1994 | Kusuhara | 623/2 |
| 5,450,860 A | 9/1995 | O'Connor | 128/898 |
| 5,571,215 A | 11/1996 | Sterman et al. | 623/66 |
| 5,593,424 A | 1/1997 | Northrup III | 606/232 |
| 5,607,471 A | 3/1997 | Seguin et al. | 623/2 |
| 5,640,955 A | 6/1997 | Ockuly et al. | 128/642 |
| 5,669,919 A | 9/1997 | Sanders et al. | 606/148 |
| 5,674,279 A | 10/1997 | Wright et al. | 623/2 |
| 5,682,906 A | 11/1997 | Sterman et al. | 128/898 |
| 5,716,367 A | 2/1998 | Koike et al. | 606/144 |

(List continued on next page.)

FOREIGN PATENT DOCUMENTS

| | | |
|---|---|---|
| WO | WO99/00059 | 1/1999 |
| WO | WO00/03759 | 1/2000 |
| WO | WO 00/60995 | 10/2000 |

OTHER PUBLICATIONS

Liddicoat et al., U.S. patent application Pub. No. 2002/0042621 entitled, "Automated Annular Plication for Mitral Valve Repair".

Oz et al., U.S. patent application Pub. No. 2001/0005787 entitled, "Method and Apparatus for Circulatory Valve Repair".

Grimes, U.S. patent application Pub. No. 2002/0026216 entitled, "Devices and Methods for Percutaneous Mitral Valve Repair".

Goldfarb et al., U.S. patent application Pub. No. 2002/0013571 entitled, "Methods and Device for Capturing and Fixing Leaflets in Valve Repair".

(List continued on next page.)

Primary Examiner—Corrine McDermott
Assistant Examiner—William H. Matthews
(74) Attorney, Agent, or Firm—Ritter, Lang & Kaplan LLP

(57) ABSTRACT

The present invention relates to a minimally invasive method of performing annuloplasty. According to one aspect of the present invention, a method for performing a procedure on a mitral valve of a heart includes inserting an implant into a left ventricle and orienting the implant in the left ventricle substantially below the mitral valve. The implant and tissue around the mitral valve are connected and tension is provided to the implant, in one embodiment, in order to substantially reduce an arc length associated with the mitral valve. In another embodiment, the implant is inserted into the left ventricle through the aorta and the aortic valve.

11 Claims, 15 Drawing Sheets

U.S. PATENT DOCUMENTS

| | | | |
|---|---|---|---|
| 5,716,397 A | 2/1998 | Myers | 623/2 |
| 5,716,399 A | 2/1998 | Love | 623/2 |
| 5,776,189 A | 7/1998 | Khalid | 623/2 |
| 5,824,066 A | 10/1998 | Gross | 623/2 |
| 5,829,447 A | 11/1998 | Stevens et al. | 128/898 |
| 5,860,920 A | 1/1999 | McGee et al. | 600/374 |
| 5,868,733 A | 2/1999 | Ockuly et al. | 606/10 |
| 5,888,240 A | 3/1999 | Carpentier et al. | 623/2 |
| 5,928,224 A | 7/1999 | Laufer | 606/27 |
| 6,102,945 A | 8/2000 | Campbell | 623/2.37 |
| 6,165,183 A | 12/2000 | Kuehn et al. | 606/139 |
| 6,210,432 B1 | 4/2001 | Solem et al. | 623/1.15 |
| 6,267,781 B1 | 7/2001 | Tu | 607/113 |
| 6,269,819 B1 | 8/2001 | Oz et al. | 128/898 |
| 6,306,133 B1 | 10/2001 | Tu et al. | 606/41 |
| 6,312,447 B1 | 11/2001 | Grimes | 606/219 |

OTHER PUBLICATIONS

Ockuly et al., U.S. patent application Publication No. 2002/0026198 entitled, "Guiding Introducers for Use in the Treatment of Accessory Path–Ways Around the Mitral Valve Using a Retrograde Approach".

Zipes, Douglas P. MD, "Ablation of Free Wall Accessory Pathways" 1994 Cather Ablation of Arrhythmias.

http://medtronic.com/cardiac/heartvalves/duran_band/.

Maisano, Francesco et al., "The Double–Orifice Technique as a Standardized Approach to Treat Mitral Regurgitation Due to Severe Myxomatous Disease: Surgical Technique".

"Anatomical Landscape of Heartport Technology", Heartport Common Stock Prospectus, Apr. 25, 1996, Cardiology Roundtable interviews.

http://www.hsforum.com/vol2/issue2/1999–4963 tables.html.

http:/www.hsforum.com/vol2/issue2/1999–4963figures.html.

Nagy, Zsolt et al., "Mitral Annuloplasty with a Suture Technique" European Journal of Cardio–Thoracic Surgery 18 (2000) 739–740.

Morales, David L.S. et al., "Development of an Off Bypass Mitral Valve Repair" Department of Surgery, Columbia University, College of Physicians and Surgeons, New York, NY.

METHOD AND APPARATUS FOR CATHETER-BASED ANNULOPLASTY

BACKGROUND OF THE INVENTION

1. Field of Invention

The present invention relates generally to techniques for treating mitral valve insufficiencies such as mitral valve leakage. More particularly, the present invention relates to systems and methods for treating a leaking mitral valve in a minimally invasive manner.

2. Description of the Related Art

Congestive heart failure (CHF), which is often associated with an enlargement of the heart, is a leading cause of death. As a result, the market for the treatment of CHF is becoming increasingly prevalent. For instance, the treatment of CHF is a leading expenditure of Medicare and Medicaid dollars in the United States of America. Typically, the treatment of CHF enables many who suffer from CHF to enjoy an improved quality of life.

Referring initially to FIG. 1, the anatomy of a heart, specifically the left side of a heart, will be described. The left side of a heart 104 includes a left atrium 108 and a left ventricle 112. An aorta 114 receives blood from left ventricle 112 through an aortic valve 120, which serves to prevent regurgitation of blood back into left ventricle 112. A mitral valve 116 is disposed between left atrium 108 and left ventricle 112, and effectively controls the flow of blood between left atrium 108 and left ventricle 112.

Mitral valve 116, which will be described below in more detail with respect to FIG. 2a, includes an anterior leaflet and a posterior leaflet that are coupled to cordae tendonae 124 which serve as "tension members" that prevent the leaflets of mitral valve 116 from opening indiscriminately. When left ventricle 112 contracts, cordae tendonae 124 allow the anterior leaflet to open upwards until limited in motion by cordae tendonae 124. Normally, the upward limit of opening corresponds to a meeting of the anterior and posterior leaflets and the prevention of backflow. Cordae tendonae 124 arise from a columnae carnae 128 or, more specifically, a musculi papillares of columnae carnae 128.

Left ventricle 112 includes trabeculae 132 which are fibrous cords of connective tissue that are attached to wall 134 of left ventricle 112. Trabeculae 132 are also attached to an interventricular septum 136 which separates left ventricle 112 from a right ventricle (not shown) of heart 104. Trabeculae 132 are generally located in left ventricle 112 below columnae carnae 128.

FIG. 2a is a cut-away top-view representation of mitral valve 116 and aortic valve 120. Aortic valve 120 has a valve wall 204 that is surrounded by a skeleton 208a of fibrous material. Skeleton 208a may generally be considered to be a fibrous structure that effectively forms a ring around aortic valve 120. A fibrous ring 208b, which is substantially the same type of structure as skeleton 208a, extends around mitral valve 116. Mitral valve 116 includes an anterior leaflet 212 and a posterior leaflet 216, as discussed above. Anterior leaflet 212 and posterior leaflet 216 are generally thin, flexible membranes. When mitral valve 116 is closed (as shown in FIG. 2a), anterior leaflet 212 and posterior leaflet 216 are generally aligned and contact one another to create a seal. Alternatively, when mitral valve 116 is opened, blood may flow through an opening created between anterior leaflet 212 and posterior leaflet 216.

Many problems relating to mitral valve 116 may occur and these insufficiencies may cause many types of ailments. Such problems include, but are not limited to, mitral regurgitation. Mitral regurgitation, or leakage, is the backflow of blood from left ventricle 112 into the left atrium 108 due to an imperfect closure of mitral valve 116. That is, leakage often occurs when a gap is created between anterior leaflet 212 and posterior leaflet 216.

In general, a relatively significant gap may exist between anterior leaflet 212 and posterior leaflet 216 (as shown in FIG. 2b) for a variety of different reasons. For example, a gap may exist due to congenital malformations, because of ischemic disease, or because a heart has been damaged by a previous heart attack. A gap may also be created when congestive heart failure, e.g., cardiomyopathy, or some other type of distress causes a heart to be enlarged. When a heart is enlarged, the walls of the heart, e.g., wall 134 of a left ventricle, may stretch or dilate, causing posterior leaflet 216 to stretch. It should be appreciated that anterior leaflet 212 generally does not stretch. As shown in FIG. 2b, a gap 220 between anterior leaflet 212 and stretched posterior leaflet 216' is created when wall 134' stretches. Hence, due to the existence of gap 220, mitral valve 116 is unable to close properly, and may begin to leak.

Leakage through mitral valve 116 generally causes a heart to operate less efficiently, as the heart must work harder to maintain a proper amount of blood flow therethrough. Leakage through mitral valve 116, or general mitral insufficiency, is often considered to be a precursor to CHF. There are generally different levels of symptoms associated with heart failure. Such levels are classified by the New York Heart Association (NYHA) functional classification system. The levels range from a Class 1 level which is associated with an asymptomatic patient who has substantially no physical limitations to a Class 4 level which is associated with a patient who is unable to carry out any physical activity without discomfort, and has symptoms of cardiac insufficiency even at rest. In general, correcting for mitral valve leakage may be successful in allowing the NYHA classification grade of a patient to be reduced. For instance, a patient with a Class 4 classification may have his classification reduced to Class 3 and, hence, be relatively comfortable at rest.

Treatments used to correct for mitral valve leakage or, more generally, CHF, are typically highly invasive, open-heart surgical procedures. Ventricular assist devices such as artificial hearts may be implanted in a patient whose own heart is failing. The implantation of a ventricular assist device is often expensive, and a patient with a ventricular assist device must be placed on extended anti-coagulant therapy. As will be appreciated by those skilled in the art, anti-coagulant therapy reduces the risk of blood clots being formed, as for example, within the ventricular assist device. While reducing the risks of blood clots associated with the ventricular assist device is desirable, anticoagulant therapies may increase the risk of uncontrollable bleeding in a patient, e.g., as a result of a fall, which is not desirable.

Rather than implanting a ventricular assist device, bi-ventricular pacing devices similar to pace makers may be implanted in some cases, e.g., cases in which a heart beats inefficiently in a particular asynchronous manner. While the implantation of a bi-ventricular pacing device may be effective, not all heart patients are suitable for receiving a bi-ventricular pacing device. Further, the implantation of a bi-ventricular pacing device is expensive.

Open-heart surgical procedures which are intended to correct for mitral valve leakage, specifically, involve the implantation of replacement valves. Valves from animals, e.g., pigs, may be used to replace a mitral valve 116 in a human. While the use of a pig valve may relatively successfully replace a mitral valve, such valves generally wear out, thereby requiring additional open surgery at a later date. Mechanical valves, which are less likely to wear out, may also be used to replace a leaking mitral valve. However, when a mechanical valve is implanted, there is an increased risk of thromboembolism, and a patient is generally required to undergo extended anti-coagulant therapies.

A less invasive surgical procedure involves heart bypass surgery associated with a port access procedure. For a port access procedure, the heart may be accessed by cutting a few ribs, as opposed to opening the entire chest of a patient. In other words, a few ribs may be cut in a port access procedure, rather than opening a patient's sternum.

One open-heart surgical procedure that is particularly successful in correcting for mitral valve leakage and, in addition, mitral regurgitation, is an annuloplasty procedure. During an annuloplasty procedure, an annuloplasty ring may be implanted on the mitral valve to cause the size of a stretched mitral valve 116 to be reduced to a relatively normal size. FIG. 3 is a schematic representation of an annuloplasty ring. An annuloplasty ring 304 is shaped approximately like the contour of a normal mitral valve. That is, annuloplasty ring 304 is shaped substantially like the letter "D." Typically, annuloplasty ring 304 may be formed from a rod or tube of biocompatible material, e.g., plastic, that has a DACRON mesh covering.

In order for annuloplasty ring 304 to be implanted, a surgeon surgically attaches annuloplasty ring 304 to the mitral valve on the atrial side of the mitral valve. Conventional methods for installing ring 304 require open-heart surgery which involve opening a patient's sternum and placing the patient on a heart bypass machine. As shown in FIG. 4, annuloplasty ring 304 is sewn to a posterior leaflet 318 and an anterior leaflet 320 of a top portion of mitral valve 316. In sewing annuloplasty ring 304 onto mitral valve 316, a surgeon generally alternately acquires a relatively large amount of tissue from mitral tissue, e.g., a one-eighth inch bite of tissue, using a needle and thread, followed by a smaller bite from annuloplasty ring 304. Once a thread has loosely coupled annuloplasty ring 304 to mitral valve tissue, annuloplasty ring 304 is slid onto mitral valve 316 such that tissue that was previously stretched out, e.g., due to an enlarged heart, is effectively pulled in using tension applied by annuloplasty ring 304 and the thread which binds annuloplasty ring 304 to the mitral valve tissue. As a result, a gap, such as gap 220 of FIG. 2b, between anterior leaflet 320 and posterior leaflet 318 may be substantially closed off. After the mitral valve is shaped by ring 304, the anterior and posterior leaflets 320, 318 will reform to create a new contact line and will enable mitral valve 318 to appear and to function as a normal mitral valve.

Once implanted, tissue generally grows over annuloplasty ring 304, and a line of contact between annuloplasty ring 304 and mitral valve 316 will essentially enable mitral valve 316 to appear and function as a normal mitral valve. Although a patient who receives annuloplasty ring 304 may be subjected to anti-coagulant therapies, the therapies are not extensive, as a patient is only subjected to the therapies for a matter of weeks, e.g., until tissue grows over annuloplasty ring 304.

A second surgical procedure which is generally effective in reducing mitral valve leakage involves placing an edge-to-edge suture in the mitral valve. With reference to FIG. 5, such a surgical procedure, e.g., an Alfieri stitch procedure or a bow-tie repair procedure, will be described. An edge-to-edge stitch 404 is used to stitch together an area at approximately the center of a gap 408 defined between an anterior leaflet 420 and a posterior leaflet 418 of a mitral valve 416. Once stitch 404 is in place, stitch 404 is pulled in to form a suture which holds anterior leaflet 420 against posterior leaflet 418, as shown. By reducing the size of gap 408, the amount of leakage through mitral valve 416 may be substantially reduced.

Although the placement of edge-to-edge stitch 404 is generally successful in reducing the amount of mitral valve leakage through gap 408, edge-to-edge stitch 404 is conventionally made through open-heart surgery. In addition, the use of edge-to-edge stitch 404 is generally not suitable for a patient with an enlarged, dilated heart, as blood pressure causes the heart to dilate outward, and may put a relatively large amount of stress on edge-to-edge stitch 404. For instance, blood pressure of approximately 120/80 or higher is typically sufficient to cause the heart to dilate outward to the extent that edge-to-edge stitch 404 may become undone, or tear mitral valve tissue.

While invasive surgical procedures have proven to be effective in the treatment of mitral valve leakage, invasive surgical procedures often have significant drawbacks. Any time a patient undergoes open-heart surgery, there is a risk of infection. Opening the sternum and using a cardiopulmonary bypass machine has also been shown to result in a significant incidence of both short and long term neurological deficits. Further, given the complexity of open-heart surgery, and the significant associated recovery time, people who are not greatly inconvenienced by CHF symptoms, e.g., people at a Class 1 classification, may choose not to have corrective surgery. In addition, people who most need open heart surgery, e.g., people at a Class 4 classification, may either be too frail or too weak to undergo the surgery. Hence, many people who may benefit from a surgically repaired mitral valve may not undergo surgery.

Therefore, what is needed is a minimally invasive treatment for mitral valve leakage. Specifically, what is desired is a method for reducing leakage between an anterior leaflet and a posterior leaflet of a mitral valve that does not require conventional surgical intervention.

SUMMARY OF THE INVENTION

The present invention relates to a non-invasive method of performing annuloplasty. According to one aspect of the present invention, a method for performing a procedure on a mitral valve of a heart includes inserting an implant into a left ventricle and orienting the implant in the left ventricle substantially below the mitral valve. The implant may be attached to tissue near the mitral valve. In one embodiment, the implant is shortened in order to substantially reduce an arc length associated with the mitral valve. In another embodiment, the implant is inserted to the left ventricle through the aorta and the aortic valve.

In still another embodiment, connecting the implant and the tissue includes introducing a catheter into the left ventricle using a guide element as a track. The catheter includes at least one pointed wire which carries a coupling element and has a tip section that may be substantially pushed through the implant and the tissue to substantially couple the implant with the tissue. In such an embodiment, the coupling element may be a T-bar.

Performing an annuloplasty on a mitral valve by accessing the left ventricle of the heart using a catheter enables complicated surgical procedures to be avoided when treating mitral valve leakage. Avoiding surgical procedures generally makes annuloplasty more accessible to patients who may benefit from annuloplasty. As mitral valve leakage is often considered to be an early indicator of congestive heart failure, a non-invasive annuloplasty procedure which corrects for leakage problems may greatly improve the quality of life of many patients who might not be suitable for invasive annuloplasty procedures.

According to another aspect of the present invention, a method for accessing the left ventricle of a heart includes introducing an elongated body into the aorta, and passing at least a portion of the elongated body through the aortic valve. Once the portion is passed through the aortic valve, the portion is located, or positioned, in the left ventricle. In one embodiment, locating the portion in the left ventricle involves positioning the portion in the space between a plane associated with the mitral valve and a plane associated with the papillary muscles of the left ventricle. In such an embodiment, the elongated body may be an implant, and locating the portion in the left ventricle may further involve positioning the implant substantially against tissue near the mitral valve.

In accordance with still another aspect of the present invention, a method for performing annuloplasty includes accessing the left ventricle to provide an implant such as a tensionable arrangement to the left ventricle. Once the left ventricle is accessed, the tensionable arrangement is coupled to fibrous tissue around a mitral valve of the heart. The tensionable arrangement is coupled to a ventricular side of the mitral valve. Finally, the tensionable arrangement is tensioned such that it substantially reduces an arc length associated with the mitral valve. In one embodiment, the tensionable arrangement is an implant, and tensioning the tensionable arrangement involves substantially collapsing the implant.

According to yet another aspect of the present invention, a device which is suitable for use in an annuloplasty procedure includes a structure, a mesh, and a tensioning element. The structure is a spring-like element that is configured to be compressed onto itself when tension is applied. The mesh is a woven mesh that is arranged over the structure, and the tensioning element is arranged to apply tension to the structure. The device is such that when the device is coupled to fibrous tissue in proximity to the mitral valve of a heart, the tensioning element causes the device to reduce an arc length associated with the mitral valve. In one embodiment, device is suitable for being coupled to a ventricular side of the mitral valve. In another embodiment, the device includes a coupler which extends through the structure and the mesh to couple the device to the fibrous tissue. In such an embodiment, the coupler may take the form of a T-bar.

In accordance with still another aspect of the present invention, a device for use in an annuloplasty procedure includes a compressible member and a shortening device. The compressible member is movable between an open uncompressed position for insertion into a left ventricle through a catheter and a closed position. The shortening device is operable to move the compressible member between the open uncompressed position and the closed position. In general, the device is positioned to reduce an opening of a mitral valve. In one embodiment, the device also includes mesh covering that extends over at least a portion of the compressible member.

These and other advantages of the present invention will become apparent upon reading the following detailed descriptions and studying the various figures of the drawings.

BRIEF DESCRIPTION OF THE DRAWINGS

The invention may best be understood by reference to the following description taken in conjunction with the accompanying drawings in which.

DETAILED DESCRIPTION OF THE EMBODIMENTS

Invasive, open-heart surgical procedures are generally effective in the treatment of mitral valve leakage. However, open-heart surgical procedures may be particularly hazardous to some patients, e.g., frail patients or patients who are considered as being very ill, and undesirable to other patients, e.g., patients who are asymptomatic and do not wish to undergo a surgical procedure. As such, open-heart surgical procedures to correct mitral valve leakage or, more generally, mitral valve insufficiency, are not suitable for many patients who would likely benefit from reducing or eliminating the mitral valve leakage.

A catheter-based annuloplasty procedure enables annuloplasty to be performed on a patient without requiring that the patient undergo open-heart surgery, or be placed on cardiopulmonary bypass. Catheters may be introduced into the left ventricle of a heart through the aorta to position a guide wire and an implant on the ventricular side of a mitral valve, i.e., under a mitral valve. Catheters may also be used to couple the implant to fibrous tissue associated with the skeleton of the heart around the mitral valve, and to reduce leakage between an anterior leaflet of the mitral valve and a posterior leaflet of the mitral valve by applying tension to the implant.

The use of catheters to perform an annuloplasty procedure enables the annuloplasty procedure to be performed without open-heart surgery, and without a bypass procedure. Recovery time associated with the annuloplasty, as well as the risks associated with annuloplasty, may be substantially minimized. As a result, annuloplasty becomes a more accessible procedure, since many patients who might previously not have received treatment for mitral valve leakage, e.g., frail patients and asymptomatic patients, may choose to undergo catheter-based annuloplasty.

Figure 6A:
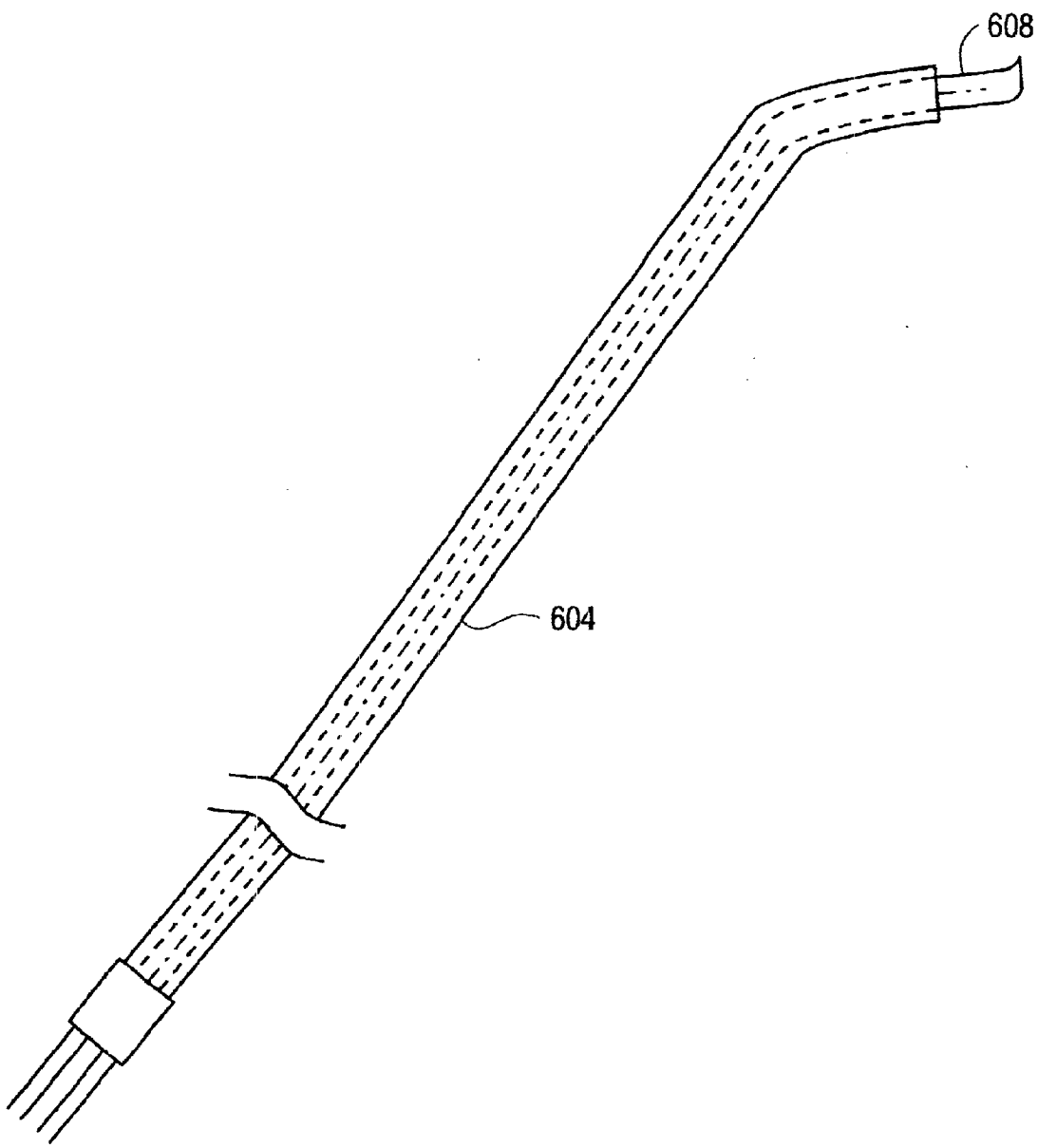
FIG. 6a is a representation of a delivery tube and a J-catheter in accordance with an embodiment of the present invention.

To begin a catheter-based annuloplasty procedure, a delivery tube and a J-catheter may be inserted into a left ventricle of the heart through the aorta. Inserting the delivery tube and the J-catheter through the aorta enables the left ventricle of the heart to be reached substantially without coming into contact with trabeculae or the cordae tendonae in the left ventricle. FIG. 6a is a diagrammatic representation of a delivery tube and a J-catheter in accordance with an embodiment of the present invention. Delivery tube 604 has a substantially circular cross section, and is configured to receive a J-catheter 608. J-catheter 608 is arranged to move longitudinally through and opening in delivery tube 604 as needed.

In general, delivery tube 604 is an elongated body which may be formed from a flexible, durable, biocompatible material such as nylon, urethane, or a blend of nylon and urethane, e.g., PEBAX®. Likewise, J-catheter 608, which is also an elongated body, may also be formed from a biocompatible material. A material used to form J-catheter 608 is typically also relatively flexible. In the described embodiment, a tip of J-catheter 608 is rigid enough to allow the tip of J-catheter 608 to maintain a relatively curved shape, e.g., a "J" shape. The curve in J-catheter 608 is configured to facilitate the positioning of a gutter catheter, as will be described below with respect to FIGS. 7a–c.

Figure 6B:
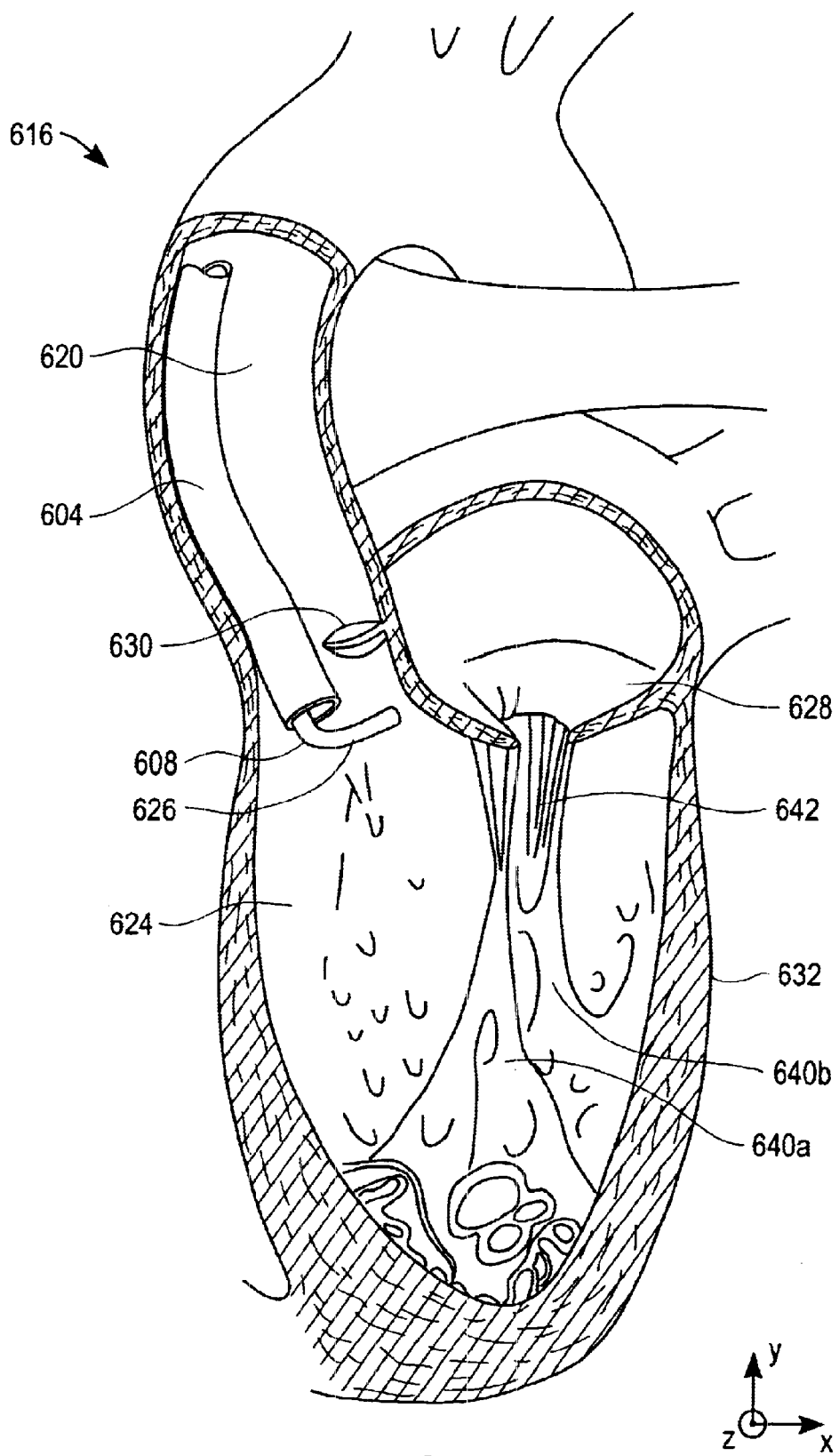
FIG. 6b is a cut-away front view of the left side of a heart in which the delivery tube and the J-catheter of FIG. 6a have been inserted in accordance with an embodiment of the present invention.

FIG. 6b is a schematic representation of delivery tube 604 and J-catheter 608 positioned within a heart in accordance with an embodiment of the present invention. As shown, after delivery tube 604 and J-catheter 608 are effectively "snaked" or inserted through a femoral artery, portions of delivery tube 604 and of J-catheter 608 are positioned within an aorta 620 of a heart 616. A tip 626 of J-catheter 608, which is substantially oriented at a right angle from the body of J-catheter 608, and an end of delivery tube 604 are oriented such that they pass through an aortic valve 630. Hence, an end of delivery tube 604 and tip 626 are positioned at a top portion of left ventricle 624, where wall 632 of left ventricle 624 is relatively smooth. The relative smoothness of the top portion of left ventricle 624 enables a catheter to be properly positioned within left ventricle 624 by guiding the tip of the catheter along wall 632. In one embodiment, tip 626 is oriented such that it is positioned approximately just below a mitral valve 628 on the ventricular side of mitral valve 628.

Once positioned within left ventricle 624, J-catheter 608 may be rotated within delivery tube 604 such that tip 626 is may enable a gutter catheter fed therethrough to run along the contour of wall 632. Typically, the gutter catheter runs along the contour of wall 632 in an area that is effectively defined between a plane associated with papillary muscles 640, a plane associated with the posterior leaflet of mitral valve 628, cordae tendonae 642, and wall 632. A "gutter" is located in such an area or region and, more specifically, is positioned substantially right under mitral valve 628 where there is a relatively insignificant amount of trabeculae.

Figure 7A:
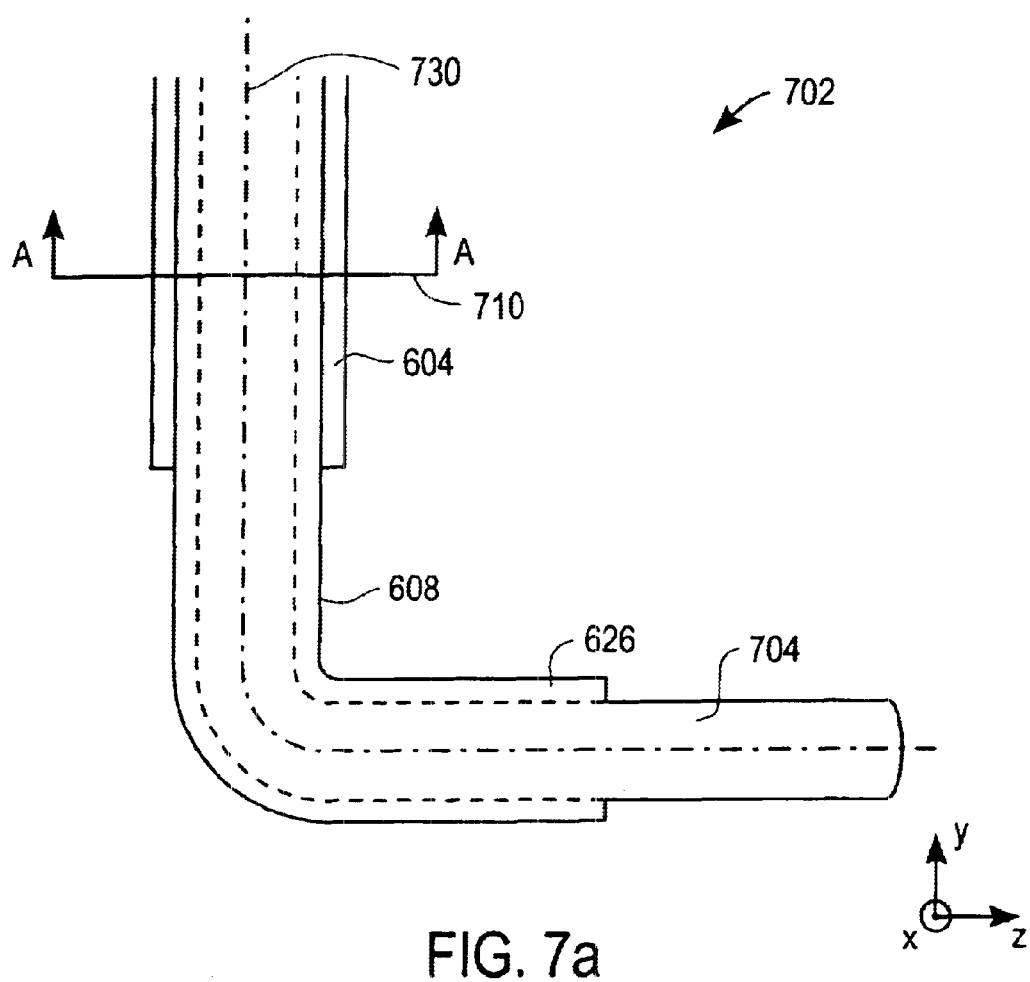
FIG. 7a is a representation of a catheter assembly in accordance with an embodiment of the present invention.
Figure 7B:
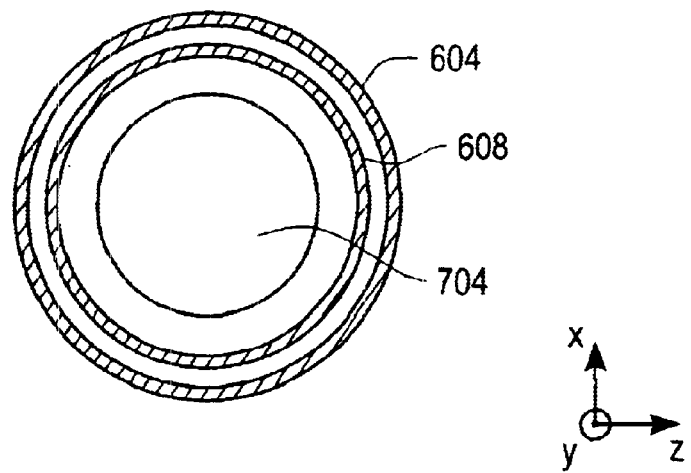
FIG. 7b is a cross-sectional representation of the catheter assembly of FIG. 7a in accordance with an embodiment of the present invention.
Figure 7C:
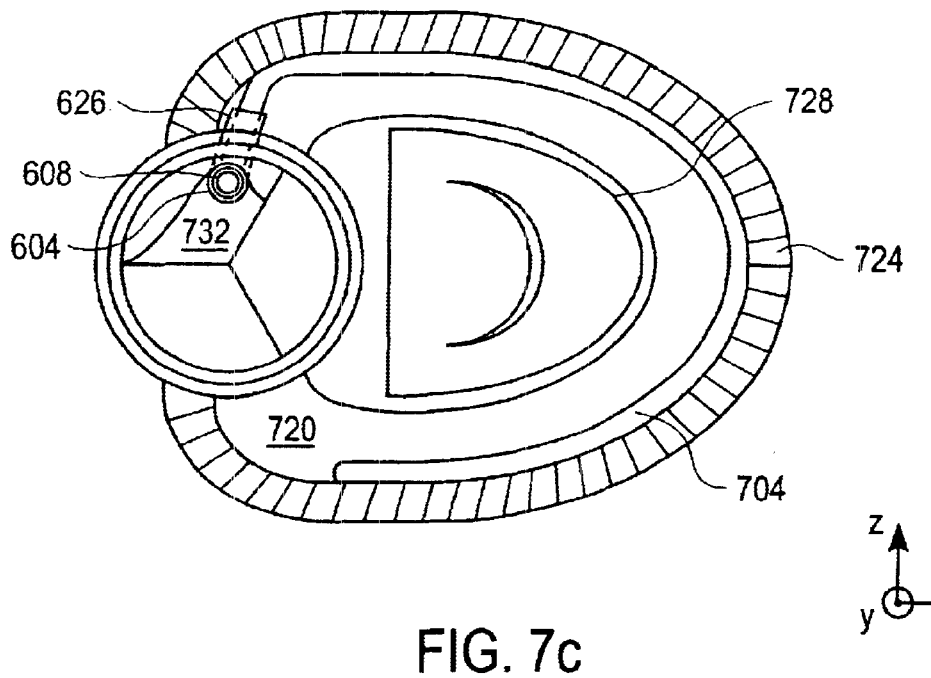
FIG. 7c is a cut-away top-view representation of a left ventricle in which the gutter catheter of FIGS. 7a and 7b has been positioned in accordance with an embodiment of the present invention.

With reference to FIGS. 7a–7c, a gutter catheter will be described in accordance with an embodiment of the present invention. A gutter catheter 704, which is part of a catheter assembly 702 as shown in FIG. 7a, is arranged to be extended through J-catheter 626 such that gutter catheter 704 may be steered within a left ventricle just beneath a mitral valve. Gutter catheter 704, which may include a balloon tip (not shown), is typically formed from a flexible material such as nylon, urethane, or PEBAX®. In one embodiment, gutter catheter 704, which is steerable, may be formed using a shape memory material.

As shown in FIG. 7a and FIG. 7b, which represents a cross section of catheter assembly 702 taken at a location 710, gutter catheter 704 is at least partially positioned within J-catheter 608 which, in turn, is at least partially positioned within delivery tube 604. Gutter catheter 704 may be free to rotate within and extend through J-catheter 608, while J-catheter 608 may be free to rotate within and extend through delivery tube 604.

Referring next to FIG. 7c, the positioning of gutter catheter 704 within a left ventricle of the heart will be described in accordance with an embodiment of the present invention. It should be appreciated that the representation of gutter catheter 704 within a left ventricle 720 has not been drawn to scale, for ease of illustration and ease of discussion. For instance, the distance between a wall 724 of left ventricle 720 and a mitral valve 728 has been exaggerated. In addition, it should also be appreciated that the positioning of delivery tube 604 and, hence, J-catheter 608 and gutter catheter 704 within aortic valve 732 may vary.

Gutter catheter 704 protrudes through tip 626 of J-catheter 608, and, through steering, essentially forms an arc shape similar to that of mitral valve 728 along the contour of a wall 724 of left ventricle 720 just beneath mitral valve 728, i.e., along the gutter of left ventricle 720. Wall 724 of left ventricle 720 is relatively smooth just beneath mitral valve 728, i.e., generally does not include trabeculae. Hence, inserting catheter assembly 702 through an aortic valve 732 into an upper portion left ventricle 720 allows gutter catheter 704 to be navigated within left ventricle 720 along wall 724 substantially without being obstructed by trabeculae or cordae tendonae.

Figure 8:
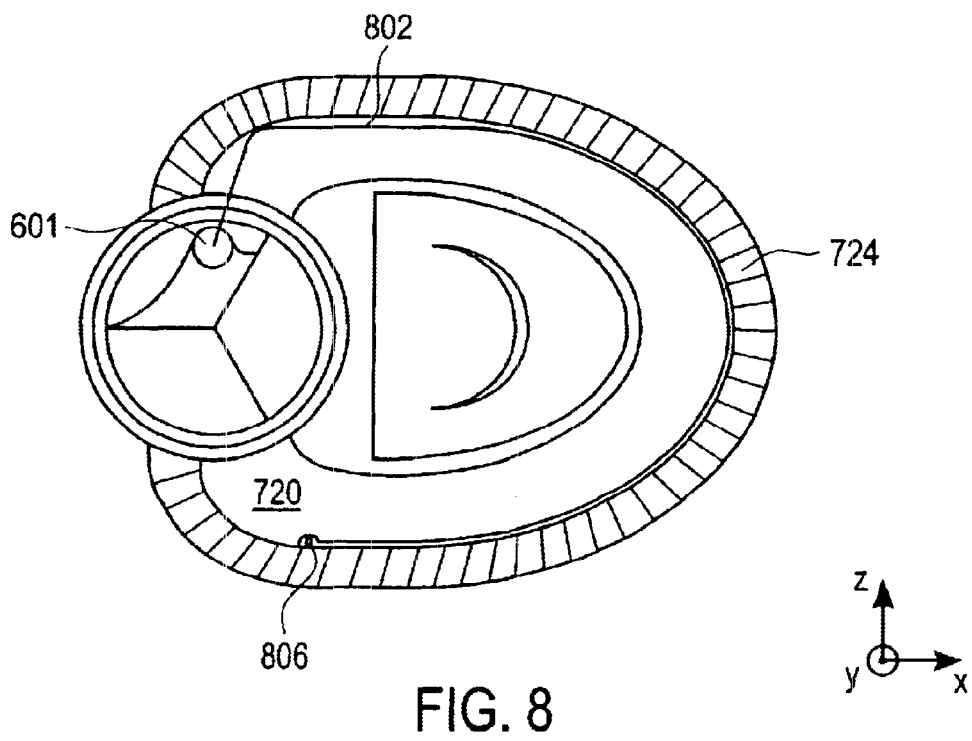
FIG. 8 is a cut-away top-view representation of a left ventricle in which a guide wire has been positioned in accordance with an embodiment of the present invention.

Gutter catheter 704 generally includes an opening or lumen (not shown) that is sized to accommodate a guide wire through which a guide wire may be inserted. The opening may be located along the central axis of gutter catheter 704, i.e., central axis 730 as shown in FIG. 7a. Delivering a guide wire through gutter catheter 704 enables the guide wire to effectively follow the contour of wall 724. In general, the guide wire may include an anchoring tip which enables the guide wire to be substantially anchored against wall 724. FIG. 8 is a diagrammatic top-view cut-away representation of a left side of a heart in which a guide wire has been positioned in accordance with an embodiment of the present invention. It should be appreciated that the representation of the left side of a heart in FIG. 8 has not been drawn to scale, and that various features have been exaggerated for ease of discussion. A guide wire 802 is positioned along wall 724 of left ventricle 720. Once guide wire 802 is inserted through gutter catheter 704 of FIGS. 7a–7c, and anchored against wall 724 using an anchoring tip 806, gutter catheter 704, along with J-catheter 708, are withdrawn from the body of the patient. It should be appreciated that delivery tube 604 typically remains positioned within the aorta after guide wire 802 is anchored to wall 724.

Figure 9A:
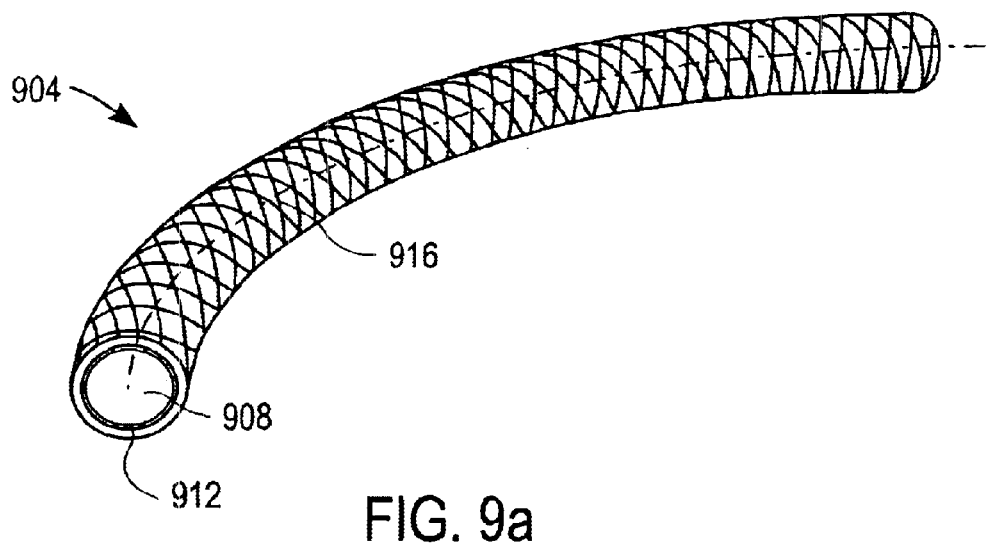
FIG. 9a is a representation of a portion of an implant in accordance with an embodiment of the present invention.

Guide wire 802, which may be formed from a material such as stainless steel or a shape memory material, is generally anchored such that guide wire 802 effectively passes along a large portion of wall 724. Typically, guide wire 802 serves as a track over which an implant may be positioned. With reference to FIG. 9a, one embodiment of an implant will be described in accordance the present invention. A section 904 of an implant includes an opening 908 therethrough which is arranged to fit over a guide wire, i.e., guide wire 802 of FIG. 8. In general, an implant is sized to be inserted through a femoral artery, an aorta, and an aortic valve. Section 904 includes a biocompatible structure 912 over which a biocompatible woven mesh 916 is placed. Mesh 916 enables mitral valve tissue regrowth to occur in and around mesh 916 once the implant is positioned under the mitral valve. While structure 912 may take a variety of different forms, in one embodiment, structure may be formed as an open spring element which may effectively be shortened or collapsed onto itself, e.g., when tension is applied to an overall implant as will be described below with respect to FIGS. 11a and 11b.

Figure 9B:
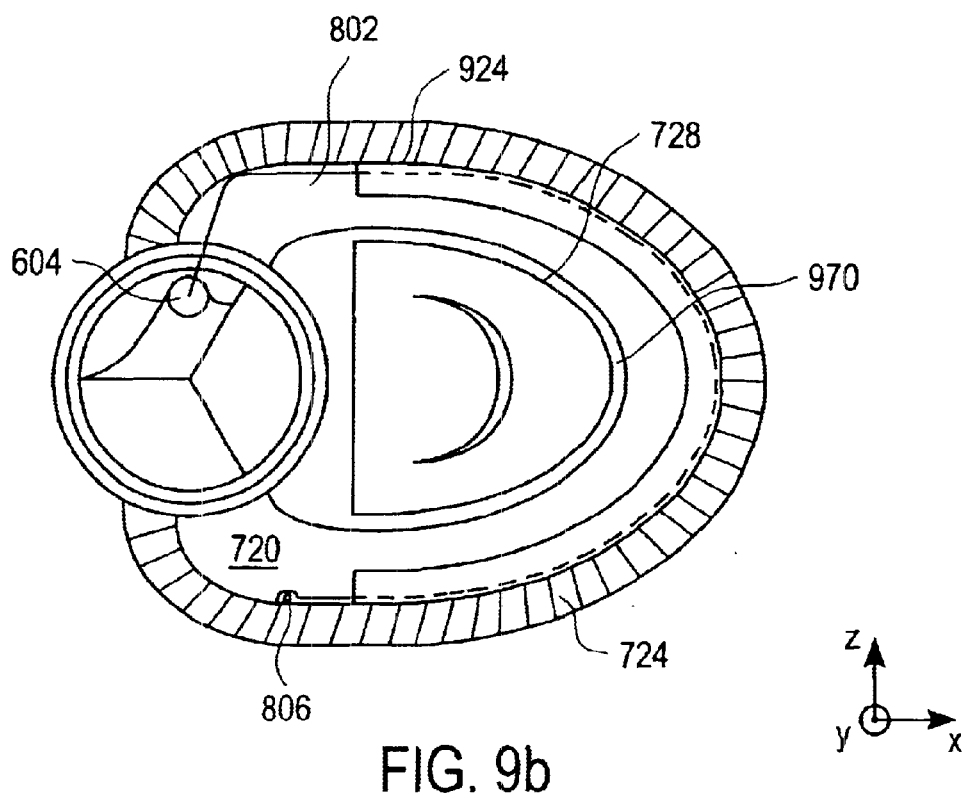
FIG. 9b is a cut-away top-view representation of a left ventricle in which an implant has been positioned in accordance with an embodiment of the present invention.

FIG. 9b is a cut-away top-view representation of a left side of a heart in which an implant has been inserted over a guide wire in accordance with an embodiment of the present invention. It should be understood that the relative dimensions of features of the portion of the heart shown in FIG. 9b are not to scale, and some dimensions have been exaggerated for purposes of discussion. An implant 924 is positioned over guide wire 802 such that implant 924 substantially follows the curved contour of mitral valve 728 and, hence, fibrous tissue 970 around mitral valve 728. That is, implant 924 is shaped approximately like a horseshoe. Guide wire 802 effectively supports implant 924 to position implant 924 substantially below mitral valve 728 in left ventricle 720.

Figure 1:
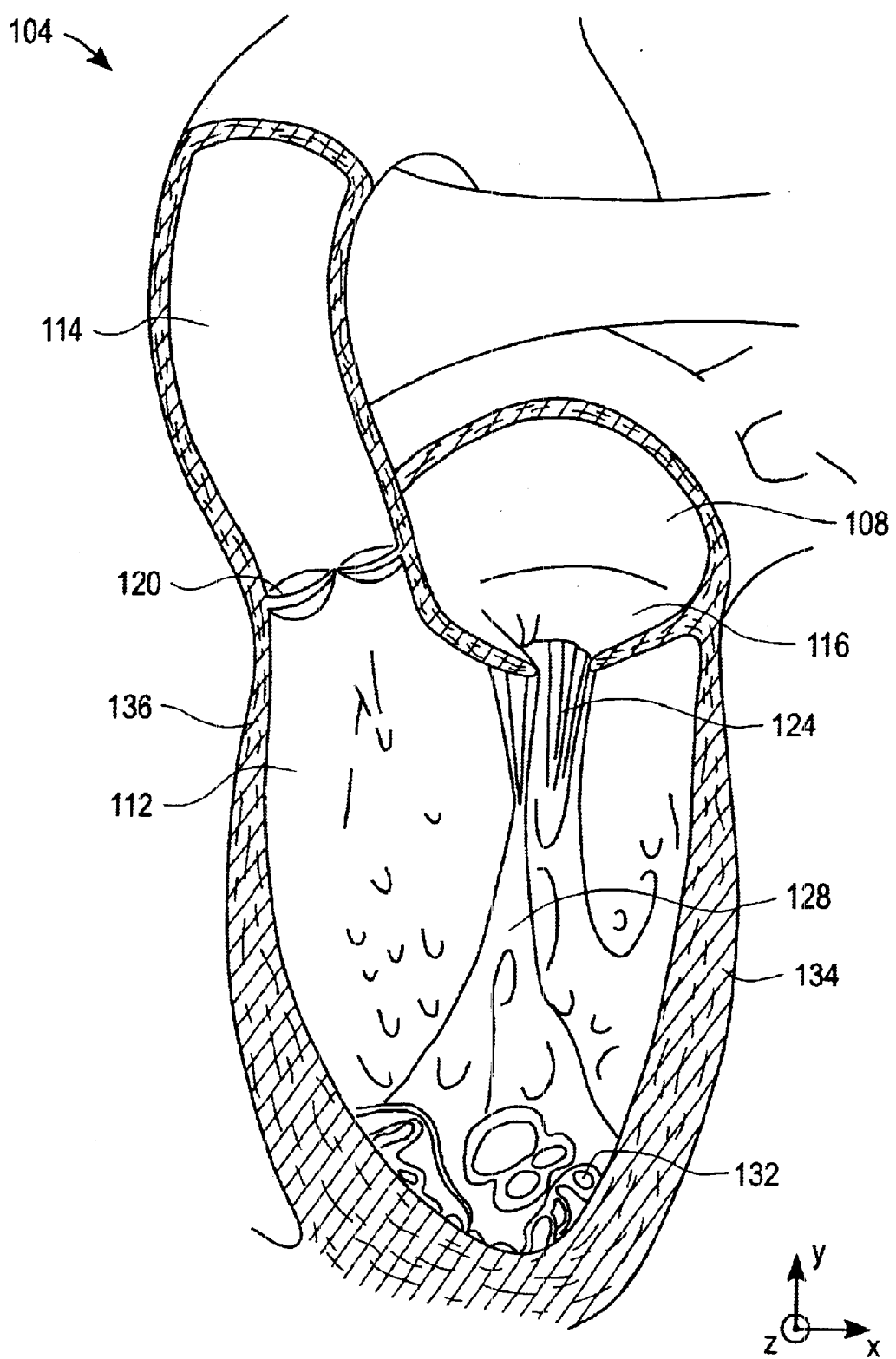
FIG. 1 is a cross-sectional front-view representation of the left side of a human heart.
Figure 2A:
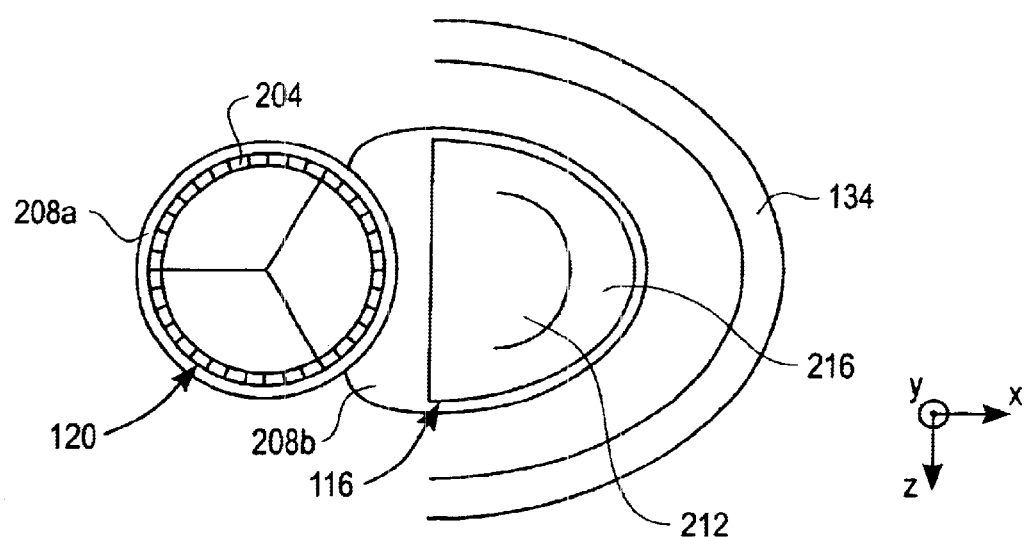
FIG. 2a is a cut-away top-view representation of the mitral valve and the aortic valve of FIG. 1.
Figure 2B:
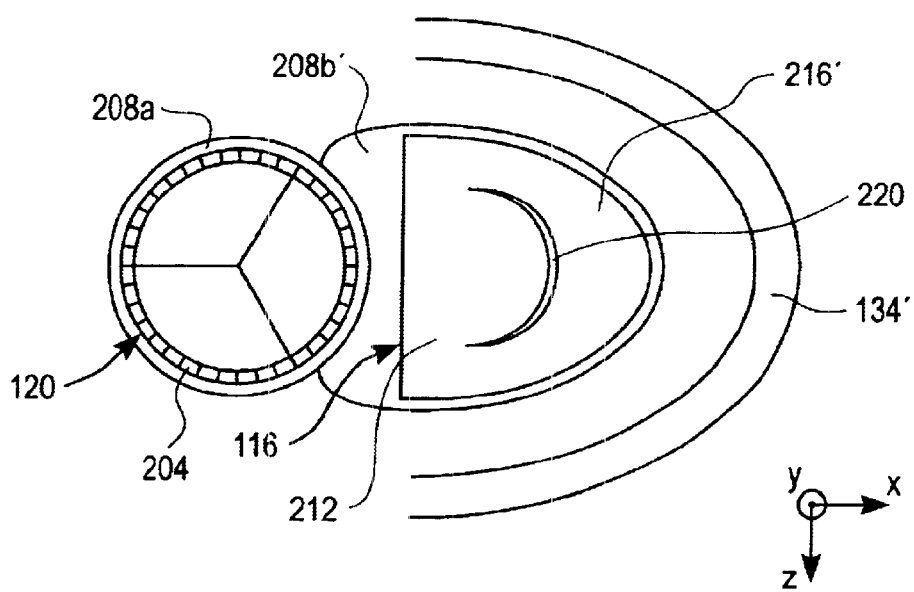
FIG. 2b is a cut-away representation of a stretched mitral valve and an aortic valve.
Figure 3:
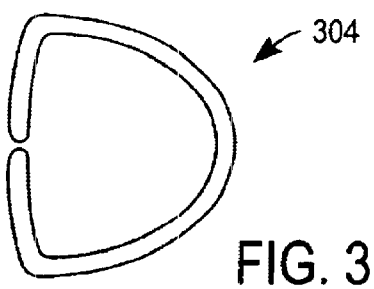
FIG. 3 is a representation of an annular ring that is suitable for use in performing a conventional annuloplasty procedure.
Figure 4:
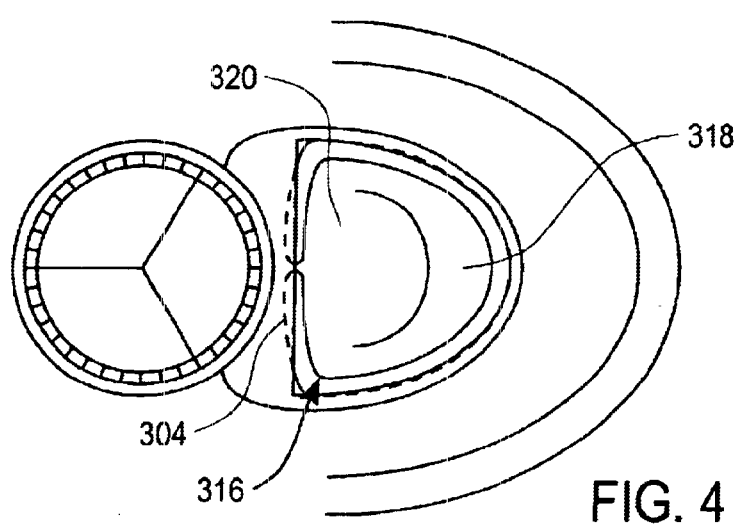
FIG. 4 is a representation of a mitral valve and an aortic valve after the annular ring of FIG. 3 has been implanted.
Figure 5:
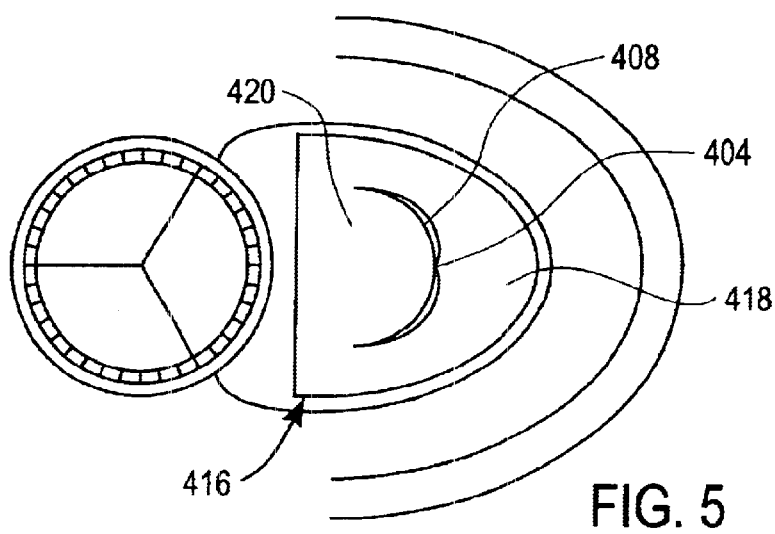
FIG. 5 is a representation of a mitral valve and an aortic valve after a single edge-to-edge suture has been applied to reduce mitral regurgitation.
Figure 9C:
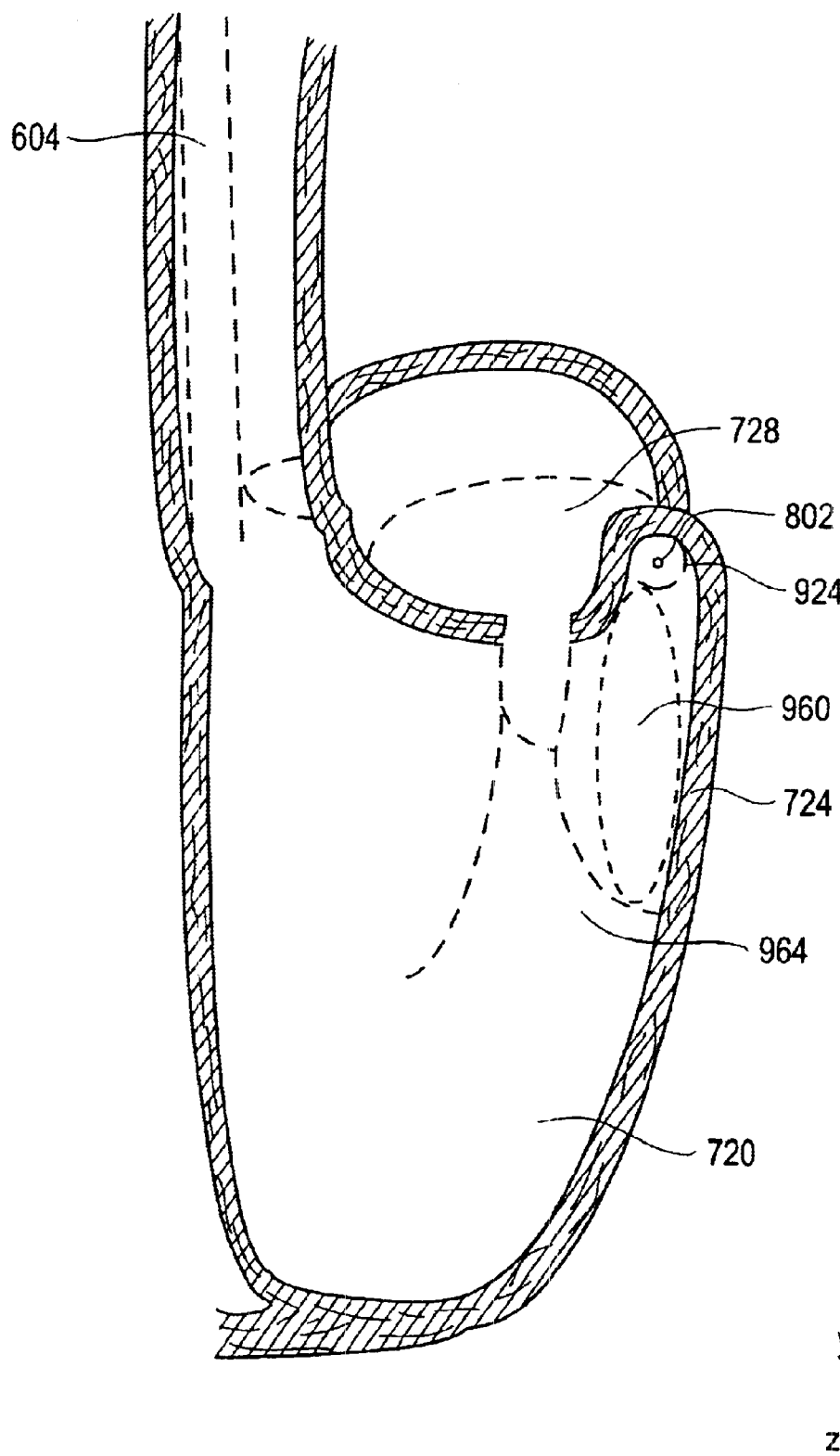
FIG. 9c is a cross-sectional front-view representation of a left ventricle in which the implant of FIG. 9b and a balloon have been inserted in accordance with an embodiment of the present invention.

As discussed above with respect to FIG. 5, implant 924 may be coupled to a balloon or balloons which may be inflated to effectively push implant 924 up against a bottom side of mitral valve 728. With reference to FIG. 9c, the positioning of implant 924 against the bottom side of mitral valve 728 will be described in accordance with an embodiment of the present invention. FIG. 9c is a diagrammatic cross-sectional side view representation of a left side of a heart. A balloon 960, which is generally coupled to implant 924, may be inflated once implant 924 is positioned over guide wire 802. Balloon 960, once inflated, substantially fills space in left ventricle 720 between mitral valve 728 and a papillary muscle 964. Inflating balloon 960 enables the pressure within balloon 960 to effectively force implant 924 against fibrous tissue 970 of the fibrous ring around mitral valve 728. In one embodiment, balloon 960 is formed from an elastomeric material.

Once implant 924 is suitably positioned, a T-bar delivery catheter may be inserted through implant 924, as mentioned above with respect to FIG. 5. Although a T-bar delivery catheter is described as providing T-bars which are suitable for coupling implant 924 to fibrous tissue 970 associated with the fibrous ring around mitral valve 728, it should be understood that other methods may be used to couple implant 924 to tissue. Substantially any mechanism or device which may reliably hold tissue may be used. Suitable devices include, but are not limited to, anvil arrangements, staples, clips, barbs, and sutures.

Figure 10:
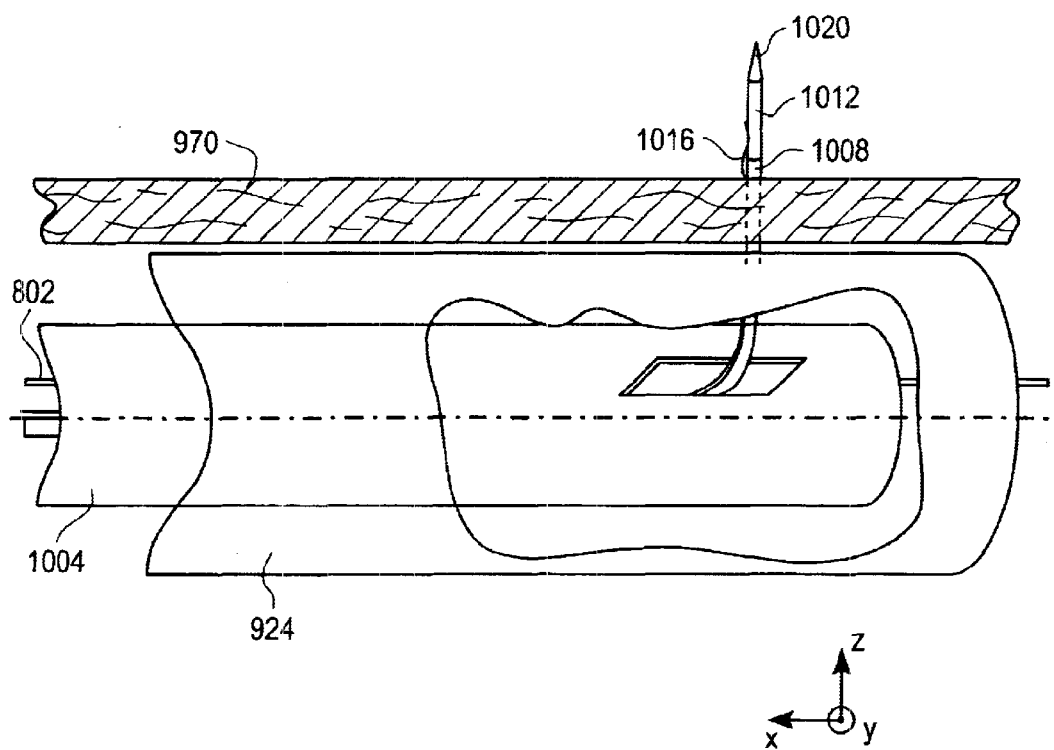
FIG. 10 is a representation of a T-bar delivery catheter in accordance with an embodiment of the present invention.

Referring next to FIG. 10, one embodiment of a T-bar delivery catheter will be described in accordance with an embodiment of the present invention. A T-bar delivery catheter 1004 may be positioned over guide wire 802 and within implant 924. It should be appreciated that T-bar delivery catheter 1004 and implant 924 have not been drawn to scale. Within delivery catheter 1004 is a wire 1008 which carries a T-bar 1012. T-bar 1012 is coupled to an extension 1016 which may be used to effectively tie off T-bar 1012 such that T-bar 1012 holds implant 924 against fibrous tissue 970 around the mitral valve. Typically, a pointed or sharpened end 1020 of wire 1008 penetrates both implant 924 and fibrous tissue 970. Once end 1020 and T-bar 1012 are both located above fibrous tissue 970, wire 1008 maybe retracted, while T-bar 1012 remains above fibrous tissue 970, i.e., on an atrial side of fibrous tissue 970. Retracting wire 1008 and, in one embodiment, delivery catheter 1004, entirely out of a patient enables an additional T-bar to be loaded onto wire 1008. Once an additional T-bar is positioned on wire 1008, wire 1008 may be reinserted into delivery catheter 1004, and delivery catheter 1004 may be used to enable another location along implant 924 to be essentially attached to fibrous tissue 970.

In general, the number of T-bars 1012 which may be used to create connections between implant 924 and fibrous tissue 970 may vary widely. By way of example, the use of approximately six or eight T-bars 1012 may be suitable, although fewer or more T-bars 1012 maybe used as necessary. After all T-bars 1012 are in place with respect to implant 924, T-bars 1012 may be tightened by tying off extensions 1016 associated with T-bars 1012.

Figure 11A:
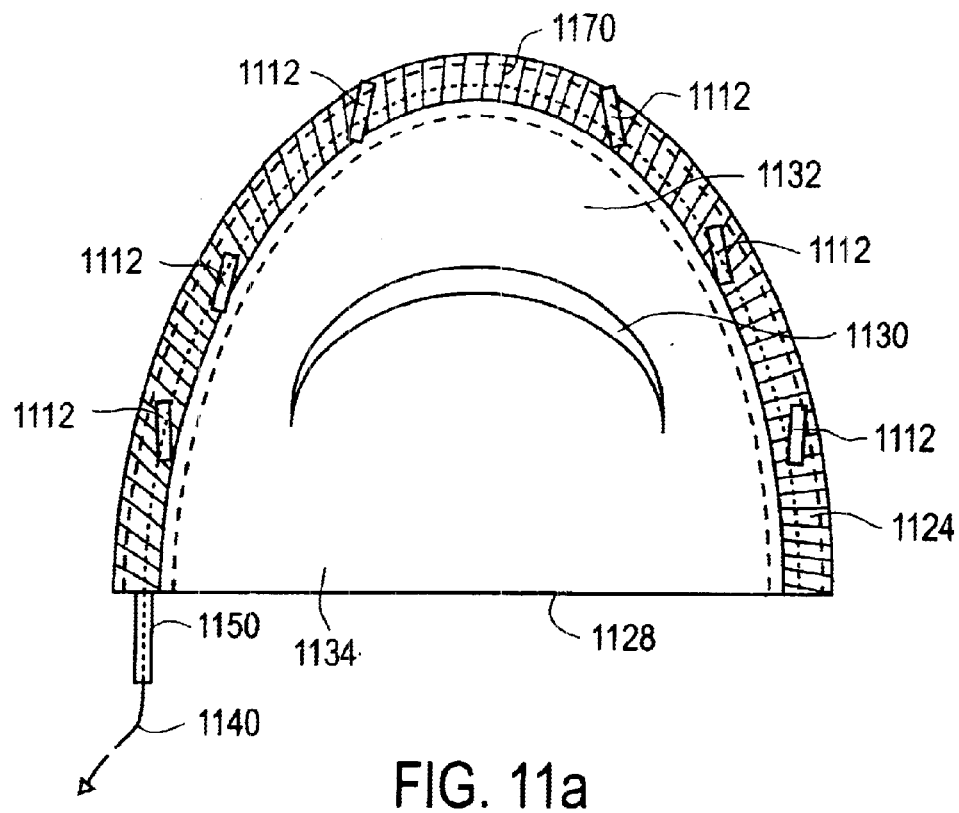
FIG. 11a illustrates an implant that is coupled to fibrous tissue around a mitral valve before tension has been applied to the implant in accordance with an embodiment of the present invention.
Figure 11B:
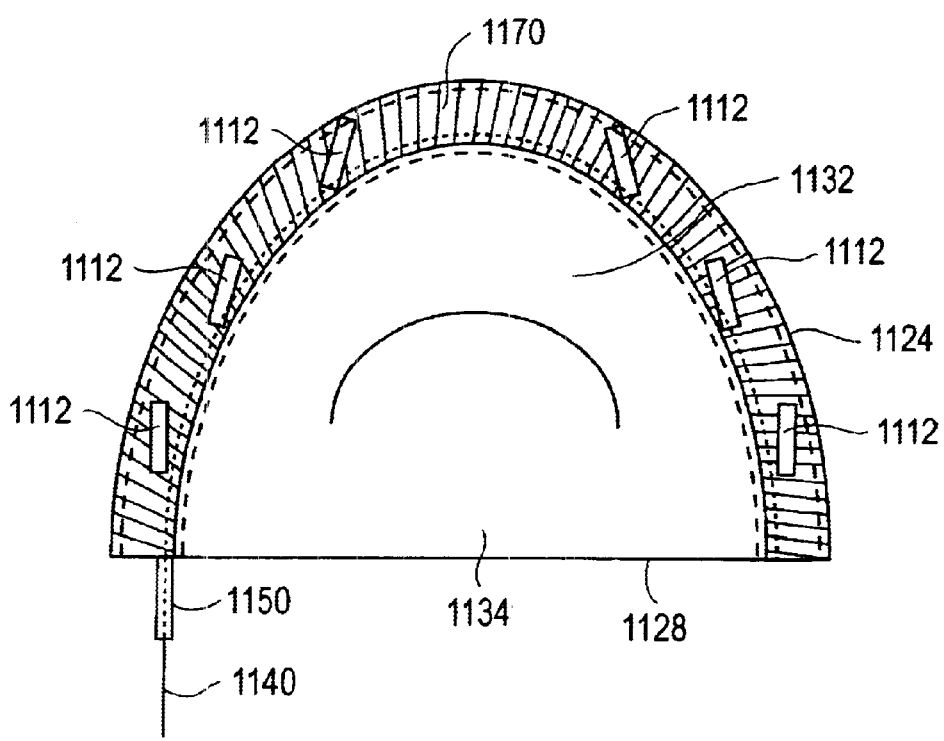
FIG. 11b illustrates the implant of FIG. 11a after tension has been applied to the implant in accordance with an embodiment of the present invention.

While T-bars 1012 create relatively intimate contact between implant 924 and fibrous tissue 970, in order to effectively shorten implant 924, i.e., to provide treatment or therapy using implant 924, implant 924 is typically tensioned. That is, the size of mitral valve 728 may be reduced by tensioning implant 924. With reference to FIGS. 11a and 11b, one method of providing tension to an implant will be described in accordance with an embodiment of the present invention. An implant 1124 is positioned under a mitral valve 1128, i.e., in a left ventricle of a heart, and is held against mitral valve 1128 using coupling devices 1112 that effectively attach implant 1124 to fibrous tissue 1170. In the described embodiment, coupling devices 1112 are T-bars, although it should be understood that other coupling devices, e.g., staples or barbs, may be used in lieu of T-bars.

In order to reduce the size of mitral valve 1128, which is stretched such that a gap 1130 is evident between a posterior leaflet 1132 and an anterior leaflet 1134, a tensioning element 1140 which is inserted within implant 1124 may be tensioned to shorten an arc length of implant 1124. Generally, tensioning element 1140 may be inserted within implant 1134 using a catheter after implant 1134 is inserted into the left ventricle. Alternatively, tensioning element 1140 may be preloaded in implant 1134. As shown, tensioning element 1140 is a string which may be pulled and ultimately tied off to effectively reduce the arc length associated with the curved outer edge of mitral valve 1128. Pulling on and tying off tensioning element 1140 may be achieved through the use of a catheter 1150 inserted within implant 1134.

When tension element 1140 is tensioned, implant 1124 effectively collapses onto itself, or is shortened. As previously mentioned, implant 1124 may be formed from a spring-like structure that is covered by a mesh. The spring-like structure is an elongated body may be collapsed onto itself or shortened when tension is applied. Hence, as shown in FIG. 11b, the arc length associated with mitral valve 1128 may be reduced, e.g., by a two-to-one ratio. Reducing the arc length associated with mitral valve 1128 allows gap 1130 to be greatly reduced. In one embodiment, gap 1130 effectively disappears such that there is no leakage of mitral valve 1128.

In one embodiment, implant 1124 is arranged to bend and to collapse onto itself such that a radius of curvature associated with implant 1124 may vary. That is, applying tension to implant 1124 allows the radius of curvature of implant 1124 to be reduced. As implant 1124 is coupled to fibrous tissue 1170 in proximity to mitral valve 1134, when the radius of curvature of implant 1124 is reduced, the size of mitral valve 1134 is also reduced.

It should be appreciated that the configuration of tensioning element 1140 be different than shown herein. While tensioning element 1140 may be a string or a similar element which may be tied off, tensioning element 1140 may also be substantially any element on which tension may be applied by pulling. Another particularly suitable tension element is a cable wrap or "zip tie," which is generally an element that may be looped onto itself and then tightened by pulling, e.g., through the use of a catheter such as catheter 1150 of FIG. 11a. Releasing such an element after pulling generally does not significantly alter the tension associated with the element.

Tensioning element 1140, in cooperation with an adjustable, or collapsible, implant 1124 allows implant 1124 to be continually adjusted as needed. By way of example, if a patient requires a readjustment of implant 1124 at some point after the initial catheter-based annuloplasty, the patient may undergo a relatively simple catheter-based procedure designed to alter the tension in implant 1124. Further, the need to select an implant 1124 for use based upon the size of a particular implant 1124 may be reduced, as an implant 1124 of a single size may be adjusted when already implanted to properly reduce the size of a stretched mitral valve 1128.

Once implant 1124 is properly adjusted, a patient may be placed on anticoagulant therapy until mitral tissue has begun to successfully grow around and into implant 1124. When tissue growth has reached a desired level, the new tissue may then effectively support implant 1124, and the patient may generally cease anticoagulant therapy. As catheter-based annuloplasty is not an open surgery and is considered to be relatively noninvasive, the recovery time from catheter-based annuloplasty is relatively short when compared to the recovery time required by conventional surgical annuloplasty procedures.

Figure 12:
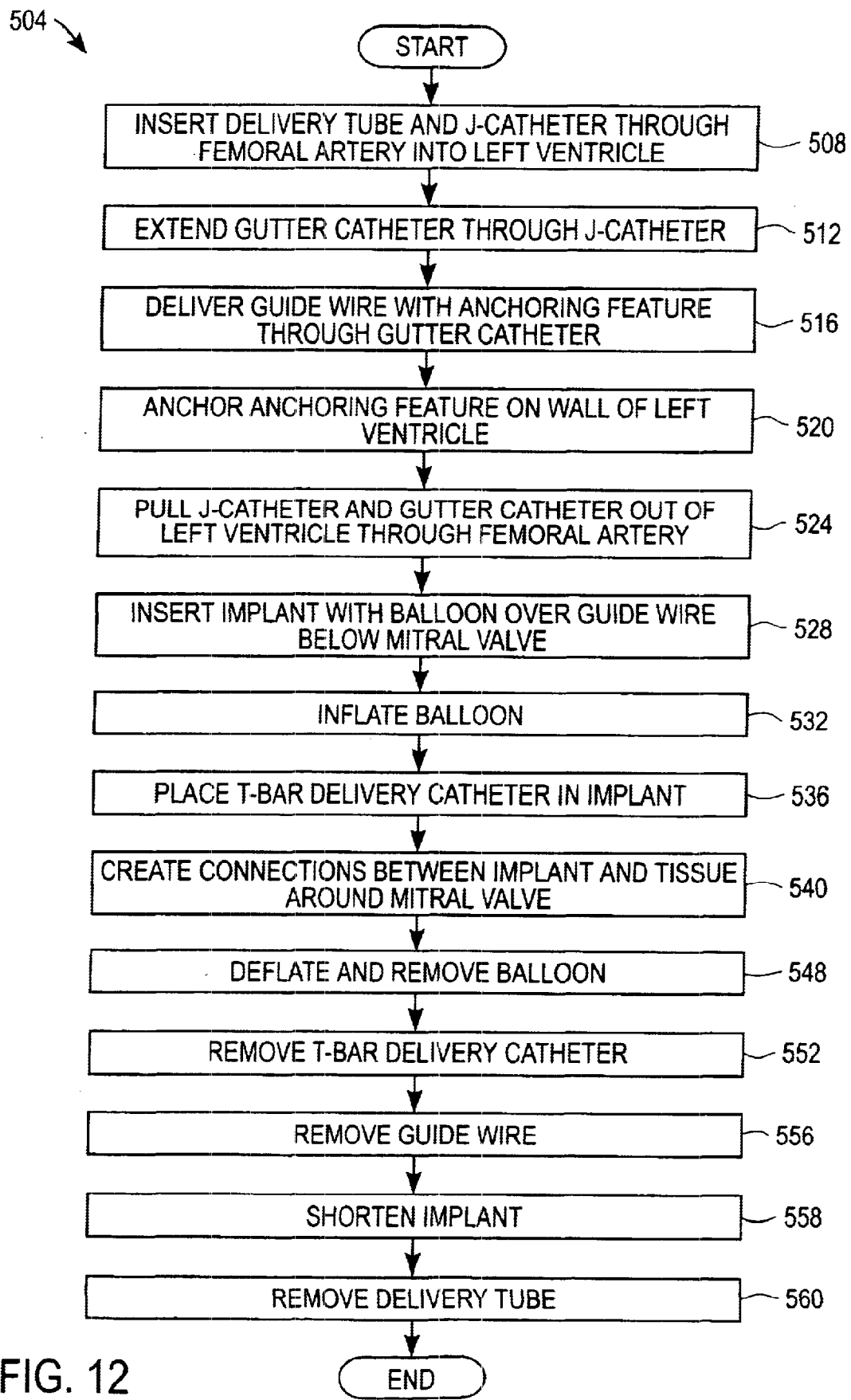
FIG. 12 is a process flow diagram which illustrates the steps associated with one method of performing annuloplasty using a catheter in accordance with an embodiment of the present invention.

With reference to FIG. 12, the performance of an annuloplasty procedure using a catheter-based system will be described in accordance with an embodiment of the present invention. Once a patient is prepared, e.g., sedated, an annuloplasty procedure 504 may begin with the insertion of a delivery tube and a J-catheter into the left ventricle of the heart of the patient. The delivery tube and the J-catheter may be inserted into the body of the patient through the femoral artery, and threaded through the femoral artery and the aorta into the left ventricle of the heart. Generally, the J-catheter is positioned within the delivery tube. One embodiment of the delivery tube and a J-catheter were described above with respect to FIGS. 6a and 6b. As will be appreciated by those skilled in the art, the delivery tube and the J-catheter are typically each threaded through the aortic valve to reach the left ventricle.

Once the delivery tube and the J-catheter are positioned within the left ventricle, a gutter catheter may be extended through the J-catheter in step 512. As was discussed above with reference to FIGS. 7a–c, the gutter catheter is arranged to effectively run against a gutter of the wall of the left ventricle substantially immediately under the mitral valve. Specifically, the gutter catheter may be positioned in the space in the left ventricle between the mitral valve and the musculi papillares, or papillary muscles. The gutter catheter often has a tip that is steerable and flexible. In one embodiment, the tip of the gutter catheter may be coupled to an inflatable balloon. The J-catheter serves, among other purposes, the purpose of allowing the gutter catheter to be initially oriented in a proper direction such that the gutter catheter may be positioned along the wall of the left ventricle.

In step 516, a guide wire with an anchoring feature may be delivered through the gutter catheter, e.g., through a lumen or opening in the gutter catheter. The guide wire is delivered through the gutter catheter such that it follows the contour of the gutter catheter against the wall of the left ventricle. After the guide wire is delivered, the anchoring feature of the guide wire is anchored on the wall of the left ventricle in step 520. Anchoring the guide wire, or otherwise implanting the guide wire, on the wall of the left ventricle enables the guide wire to maintain its position within the left ventricle.

The J-catheter and the gutter catheter are pulled out of the left ventricle through the femoral artery in step 524, leaving the guide wire anchored within the left ventricle, as was discussed above with respect to FIG. 8. Once the J-catheter and the gutter catheter are removed from the left ventricle, an implant which may be coupled to a substantially deflated balloon is inserted into the left ventricle using the guide wire as a guide track in step 528. In other words, an implant that is intended to be coupled to the mitral valve is positioned in the left ventricle under the mitral valve, i.e., on a ventricular side of the mitral valve. One suitable implant was described above with respect to FIG. 9a. In one embodiment, the implant may be inserted into the left ventricle using a catheter which may be retracted once the implant is positioned under the mitral valve in contact with the fibrous tissue around the mitral valve.

After the implant and the balloon are inserted in the left ventricle, the balloon is inflated in step 532. Inflating the elastomeric balloon at a relatively modest pressure using, for example, an air supply coupled to the balloon through the implant, serves to cause the implant to be pressed up against the fibrous tissue around the mitral valve. Generally, the inflated balloon substantially occupies the space between the mitral valve and the papillary muscles. In one embodiment, more than one balloon may be used to position the implant against the fibrous tissue around the bottom of the mitral valve.

A T-bar delivery catheter is inserted through the implant in step 536, once the balloon is inflated in step 532. The T-bar delivery catheter effectively delivers T-bars, or similar mechanisms, which are arranged to attach or otherwise couple the implant to an annulus of the mitral valve, e.g., the fibrous tissue of the skeleton around the mitral valve. In step 540, connections are created between the implant and substantially any suitable tissue near the mitral valve to effectively attach the implant to the tissue. The connections may be created by extending sharpened wires which carry elements such as T-bars through the implant and the tissue, then retracting the sharpened wires, and locking the T-bars in place, as discussed above with respect to FIG. 10.

Once a desired number of connections, e.g., six connections, are made between the implant and the tissue, then the balloon may be deflated and removed from the left ventricle in step 548. It should be understood that since the implant is effectively connected to tissue around the mitral valve, deflating the balloon does not cause the position of the implant to be significantly moved. After the balloon is deflated, the T-bar delivery catheter is removed from the left ventricle in step 522. In step 556, the guide wire may be removed. The implant is then typically shortened in step 558, as for example by providing tension to the implant. As will be appreciated by those skilled in the art, shortening the implant involves contracting the mitral valve or, more specifically, the posterior leaflet of the mitral valve. Although the implant may be shortened in substantially any suitable manner, in one embodiment, the implant may be shortened by tightening a string or a cord associated with the implant to effectively reduce the arc length associated with the implant, e.g., by a two-to-one ratio. Once the implant is successfully shortened, the delivery tube may be removed in step 560. After the delivery tube is removed, the annuloplasty procedure is completed.

Figure 13A:
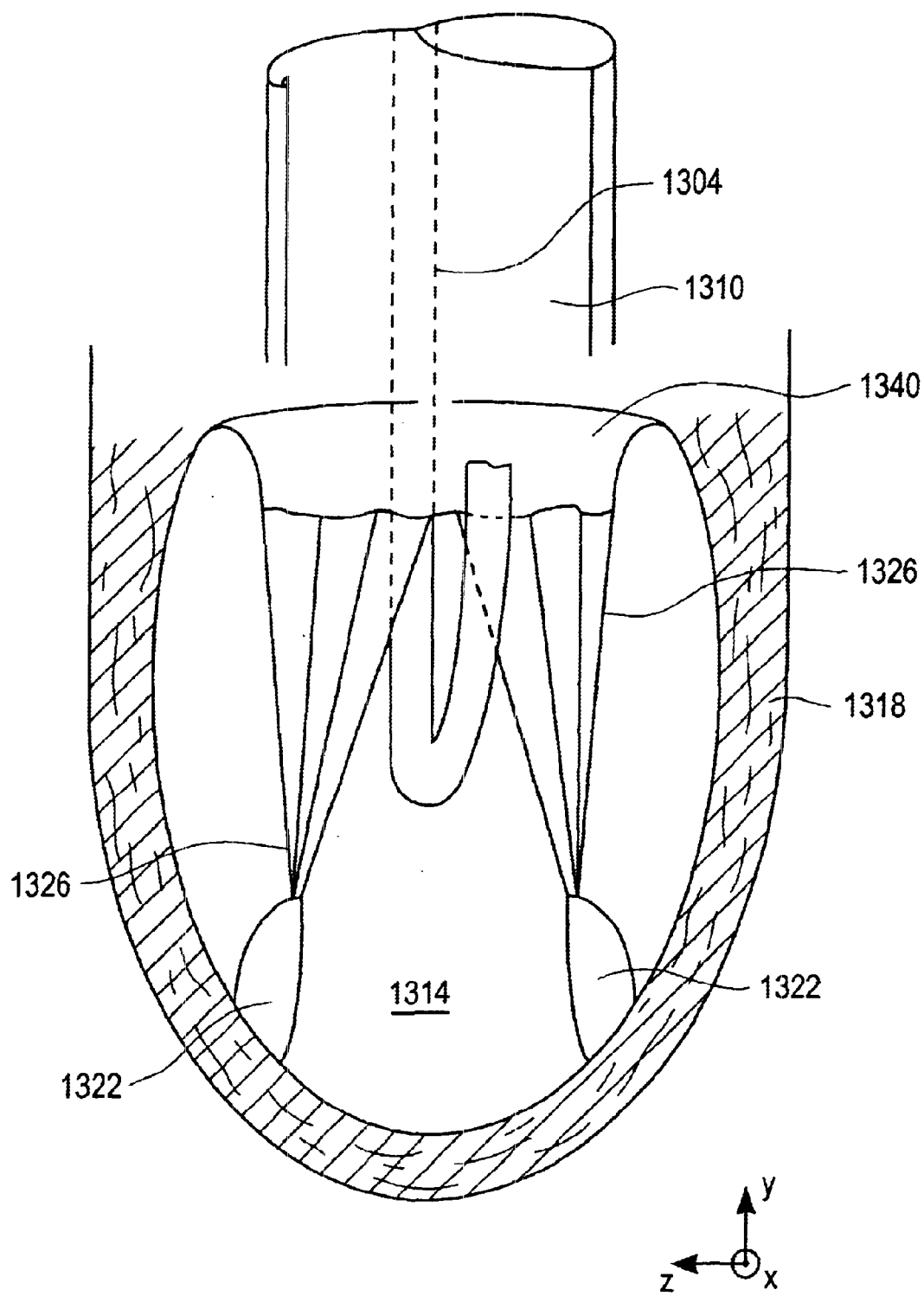
FIG. 13a is a cut-away representation of a left ventricle in which a catheter has been inserted in accordance with a second embodiment of the present invention.
Figure 13B:
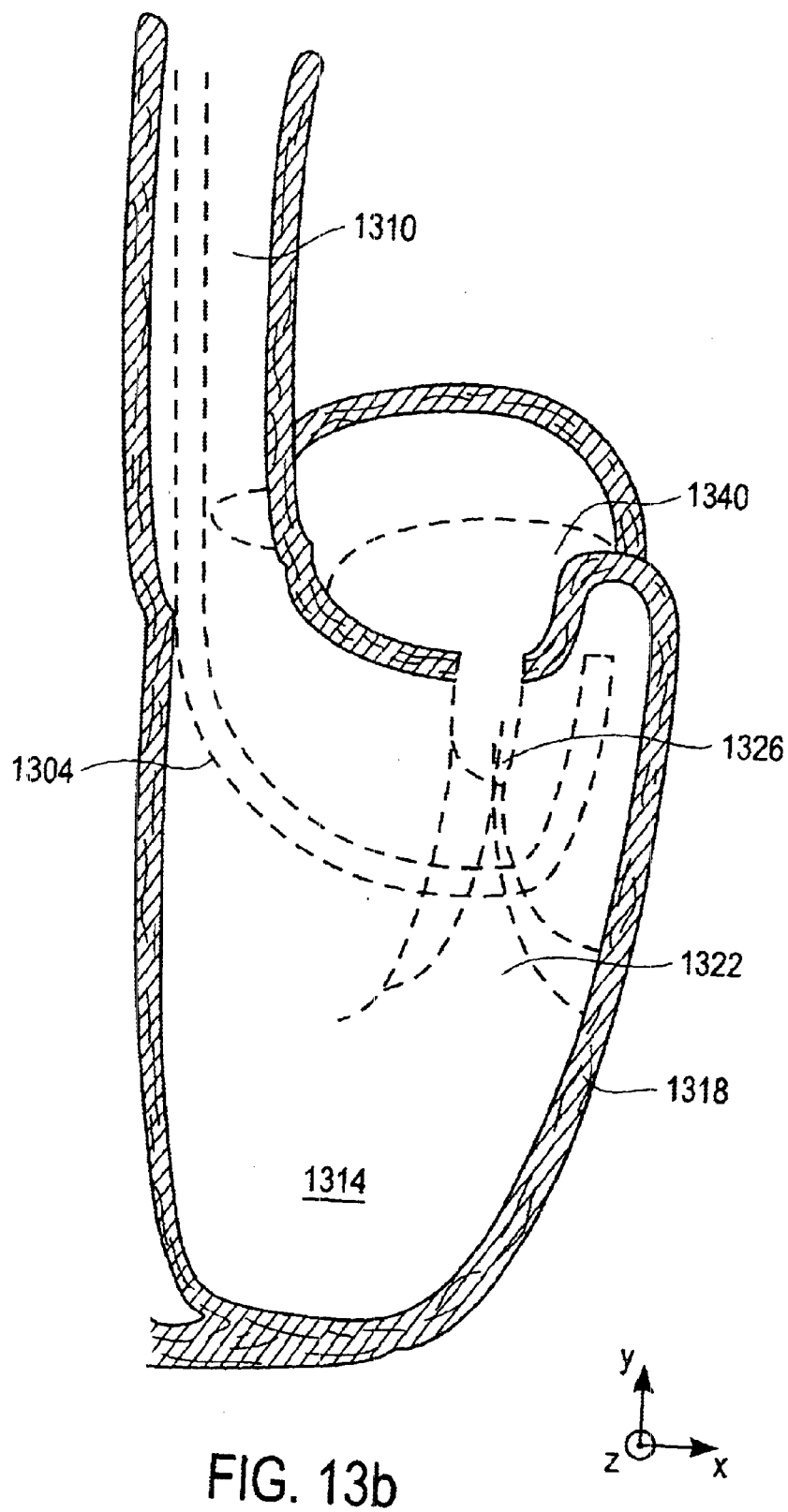
FIG. 13b is a cross-sectional representation of a left ventricle in which the catheter of FIG. 13a has been inserted in accordance with the second embodiment of the present invention.

It should be appreciated that implanting an implant in tissue near the mitral valve, then shortening the implant, is just one method of treating mitral valve leakage in a minimally invasive manner using a catheter-based system. Another method, which will be described below with respect to FIGS. 13a and 13b, involves accessing the mitral valve through the aorta and the left ventricle, and implanting a clip element which serves to effectively pinch together the anterior leaflet and the posterior leaflet of the mitral valve to reduce leakage. FIG. 13a is a schematic cut-away representation of a left ventricle of the heart in which a catheter that is suitable for use in accessing a mitral valve in accordance with a second embodiment of the present invention is positioned. FIG. 13b is a cross-sectional representation of the left ventricle and the catheter of FIG. 13a. A catheter 1304 is inserted into a left ventricle 1314 through an aortic valve 1310. Catheter 1304, which may be steerable and flexible, has a curved orientation such that catheter 1304 may pass between cordae tendonae 1326 that are coupled to papillary muscles 1322 and mitral valve 1340. That is, catheter 1304 is shaped to pass through a plane defined by papillary muscles 1322, as well as cordae tendonae 1326, to reach a posterior leaflet "side" of mitral valve 1340.

As shown, catheter 1304 does not follow the contour of a wall 1318 of left ventricle 1314, and is still positioned such that a portion of catheter 1304 is positioned in a region of left ventricle 1314 between mitral valve 1340, cordae tendonae 1326, papillary muscles 1322, and wall 1318. Hence, catheter 1304 is able to directly access a posterior leaflet of mitral valve 1340 substantially directly. A catheter 1304 which, in one embodiment, accesses a gutter portion of left ventricle 1314 may be easier to fabricate and to actively control than a catheter assembly which includes a J-catheter and a gutter catheter, e.g., J-catheter 608 and gutter catheter 704 of FIG. 7a, as catheter 1304 generally does not need to be manipulated with many direction changes. Instead, catheter 1304 may be formed to include either a curved end portion, as shown in FIG. 13b, or a v-shaped end portion which both enable an end portion of catheter 1304 to access the portion of left ventricle 1314 that is positioned substantially immediately under mitral valve 1340.

Figure 13C:
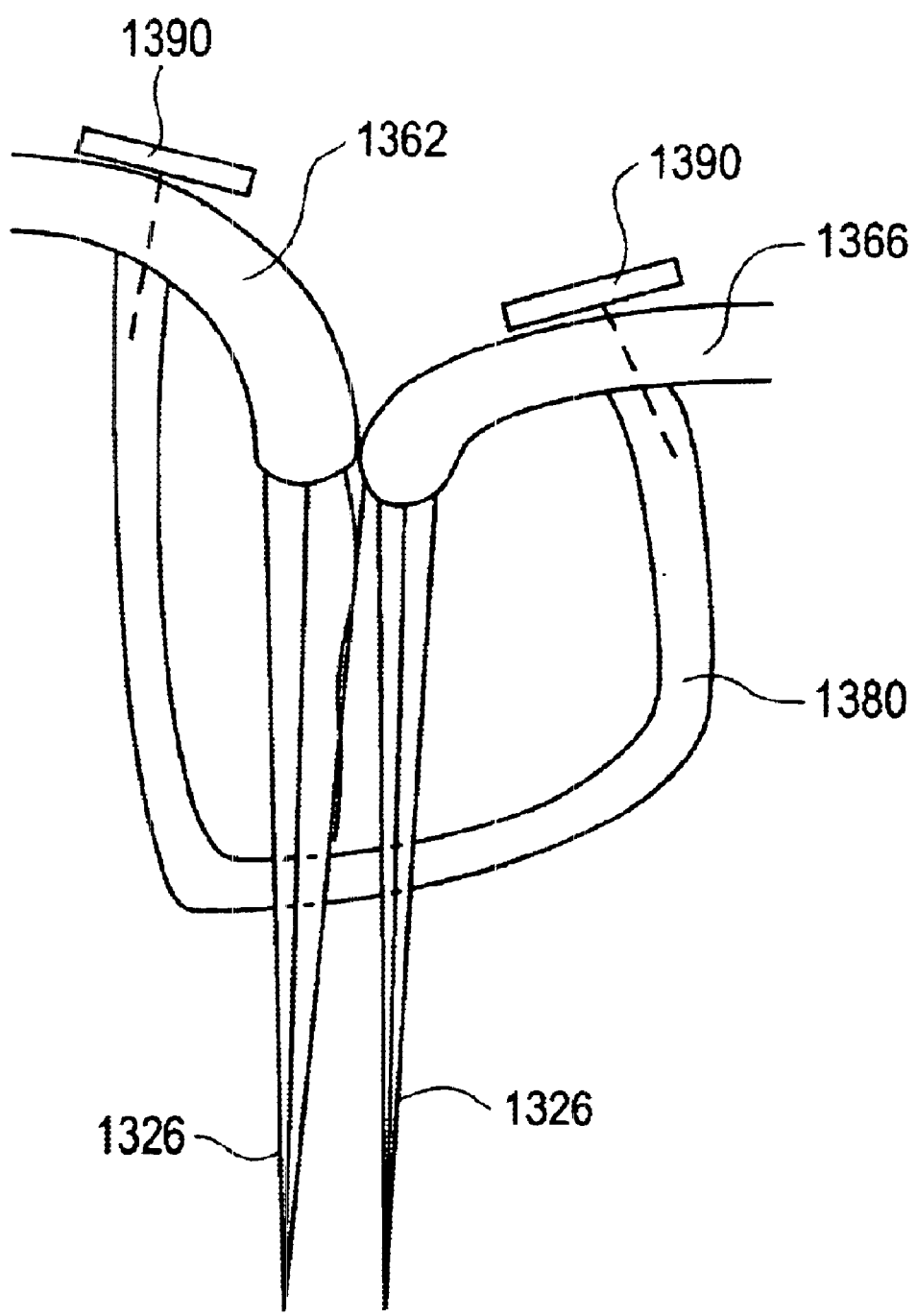
FIG. 13c is a representation of a clip which is coupled to an anterior leaflet and a posterior leaflet in accordance with the second embodiment of the present invention.

A tip portion of catheter 1304 maybe directed against mitral valve 1340, thereby facilitating the ability to place a tissue anchor or clip element which may act to pinch an anterior leaflet against a posterior leaflet. FIG. 13c is a schematic representation of a clip element positioned with respect to a posterior leaflet and an anterior leaflet of a mitral valve in accordance with a second embodiment of the present invention. It should be appreciated that the elements in FIG. 13c have not been drawn to scale for purposes of discussion. A clip 1380, which may be formed from a material such as steel, may be coupled to an anterior leaflet 1362 and a posterior leaflet 1366 of a mitral valve using catheter 1304 of FIGS. 13a and 13b. Clip 1380, which passes between cordae tendonae 1326 associated with anterior leaflet 1362 and cordae tendonae 1326 associated with posterior leaflet 1366, may be coupled to anterior leaflet 1362 and posterior leaflet 1366 using, for example, T-bar arrangements 1390.

By pinching together anterior leaflet 1362 and posterior leaflet 1366, the leakage through a gap (not shown) between anterior leaflet 1362 and posterior leaflet 1366 may be reduced. While the presence of clip 1380 may result in a patient having to undergo anticoagulant therapies, the placement of clip 1380 in lieu of an implant such as implant 924 of FIG. 9b may minimize the amount of time associated with a leakage correction process.

Although only a few embodiments of the present invention have been described, it should be understood that the present invention may be embodied in many other specific forms without departing from the spirit or the scope of the present invention. By way of example, methods of introducing an implant into the left ventricle to correct for mitral valve leakage, or mitral valve insufficiency, may be applied to introducing implants which correct for leakage in other valves. For instance, the above-described procedure may be adapted for use in repair a leaking valve associated with a right ventricle.

While connecting an implant to fibrous tissue associated with the mitral valve of the heart has generally been described, the implant may be connected to other types of tissue which are near, around, in proximity to, or include the mitral valve. Other tissues to which an implant may be connected include tissues associated with the myocardium, or tissues associated with the wall of the left ventricle. In one embodiment, the implant may be substantially directly connected to the leaflets of the mitral valve.

In general, methods of accessing a left ventricle through the aorta may be applied to procedures other than annuloplasty. The left ventricle may be accessed to perform mapping or ablation therapies, or to stabilize a patient suffering from an acute valve failure, e.g., by filling space in the left ventricle by inflating a balloon. Also, a balloon, either steady state or pulsatile, may be used to increase the ejection fraction associated with the left ventricle. The left ventricle may also be accessed in order to access the left atrium through the mitral valve. Specifically, the smooth portion of the left ventricle, e.g., the gutter, may be accessed en route to accessing the left atrium. It should be appreciated that accessing the gutter may be used in conjunction with access routes via other channels to the heart such as a coronary sinus and a transceptal approach to the left atrium.

While a balloon may be inflated within a left ventricle such that the balloon is effectively trapped under the posterior leaflet of a mitral valve to treat sudden heart failure. The balloon may remain positioned in the left ventricle until surgery is performed on the heart, at which time the balloon may be removed. In one embodiment, such a balloon may be arranged to be filled with blood that clots off, thereby enabling the balloon to become what is effectively a permanent structure in the left ventricle that reduces mitral regurgitation.

Access to the left ventricle may also facilitate the use of a camera within left ventricle. For example, a camera may be fed into the left ventricle on the tip of a catheter-like device to enable the interior of the left ventricle to be viewed to identify any anomalies which may be present in the left ventricle. It should be appreciated that such a camera may also be passed into the coronary sinus.

Rather than implanting an implant to correct for mitral valve insufficiency using a catheter-based approach, a series of local plications to the mitral valve may be used to achieve annuloplasty. By way of example, a catheter or other device that is suitable for creating local plications may be located along the wall of a left ventricle beneath the mitral valve. Local plications may be created by elements which engage fibrous tissue and close upon themselves such that tissue is engaged. Alternatively, a one-way tensioning device may be used to effectively pull in on the local plications, e.g., elements, such that the arc length of the mitral valve is effectively reduced.

Local plications may generally be created through the use of staple elements which engage each other once they penetrate the fibrous tissue, or hook-like elements. It should be appreciated, however, that in other embodiments, suture type materials may be used to create local plications.

While an implant which may effectively collapse onto itself, e.g., be shortened, when tension is applied is suitable for use in a catheter-based annuloplasty as described above, it should be appreciated that such an implant is suitable for use in a variety of different annuloplasty procedures. For instance, the implant may be used in a conventional, surgical annuloplasty procedure since its use may enable a surgeon to continuously adjust the amount by which the arc length of a mitral valve may be reduced.

An implant has generally been described as having a shape which is similar to that of a horseshoe ring. Implants of other shapes may generally be implanted within a heart to correct for mitral valve insufficiency. By way of example, an implant which has a curved shape that does not follow substantially the entire arc length of a mitral valve may be implanted without departing from the spirit or the scope of the present invention. Such an implant may generally cover a larger area than would be covered by a local plication.

It should be understood that although a guide wire has been described as including an anchoring tip to anchor the guide wire to a wall of the left ventricle, a guide wire may be anchored with respect to the left ventricle in substantially any suitable manner. By way of example, a guide wire may include an anchoring feature which is located away from the tip of the guide wire. In addition, a guide wire may more generally be any suitable guiding element which is configured to facilitate the positioning of an implant.

An elastomeric balloon has been described as being suitable for use in effectively forcing an implant against a surface to which the implant is to be connected. In lieu of an elastomeric balloon, substantially an expanding structure may be used to push the implant against a surface. By way of example, an expanding metal structure which is expandable from a closed position into an open position may be used to provide pressure or force on an implant.

While access to the gutter of the left ventricle has been described as being associated with a minimally invasive catheter annuloplasty procedure, it should be understood that the gutter of the left ventricle may also be accessed, e.g., for an annuloplasty procedure, as a part of a surgical procedure. For instance, the aorta of a heart may be accessed through an open chest surgical procedure before a catheter is inserted into the aorta to reach the left ventricle. Alternatively, an implant may be introduced on a ventricular side of a mitral valve through a ventricular wall which is accessed during an open chest surgical procedure.

The steps associated with performing a catheter-based annuloplasty may be widely varied. Steps may generally be added, removed, reordered, and altered without departing from the spirit or the scope of the present invention. Therefore, the present examples are to be considered as illustrative and not restrictive, and the invention is not to be limited to the details given herein, but may be modified within the scope of the appended claims.

What is claimed is:

1. A method for performing a procedure on a mitral valve of a heart, the method comprising:

inserting at least one implant into a left ventricle of the heart wherein inserting the implant into the left ventricle includes introducing the implant into an aorta and passing the implant through an aortic valve interposed between the aorta and the left ventricle;

introducing a guide element into the left ventricle, the guide element being configured to be positioned in the left ventricle between a plane of the mitral valve and a plane associated with papillary muscles of the heart, wherein inserting the implant into the left ventricle includes positioning the implant such that the implant uses the guide element as a track and wherein introducing the guide element into the left ventricle further includes (a) introducing a first catheter assembly into the aorta, the first catheter assembly including an angled catheter, and a gutter catheter, wherein the angled catheter substantially carries the gutter catheter, the angled catheter being arranged to facilitate positioning of the gutter catheter,(b) positioning the gutter catheter beneath the mitral valve between the plane of the mitral valve and the plane associated with the papillary muscles, wherein positioning the gutter catheter includes positioning the gutter catheter along a wall of the left ventricle, and (c) inserting the guide element into a lumen of the gutter catheter;

positioning the at least one implant with respect to the mitral valve, wherein positioning the implant includes orienting the implant in the left ventricle substantially below the mitral valve;

attaching the implant to tissue located near the mitral valve;

reducing an arc length of the implant, wherein reducing the arc length of the implant substantially reduces an arc length associated with the mitral valve; and removing the guide element from the left ventricle after attaching the implant to the tissue.

2. A method as recited in claim 1 wherein introducing the guide element into the left ventricle further includes:

anchoring the guide element against the wall.

3. A method as recited in claim 1 wherein the tissue is fibrous tissue.

4. A method for performing a procedure on a mitral valve of a heart, the method comprising:

inserting at least one implant into a left ventricle of the heart wherein inserting the implant into the left ventricle includes introducing the implant into an aorta and passing the implant through an aortic valve interposed between the aorta and the left ventricle;

introducing a guide element into the left ventricle, the guide element being configured to be positioned in the left ventricle between a plane of the mitral valve and a plane associated with papillary muscles of the heart, wherein inserting the implant into the left ventricle includes positioning the implant such that the implant uses the guide element as a track;

positioning the at least one implant with respect to the mitral valve, wherein positioning the implant includes orienting the implant in the left ventricle substantially below the mitral valve;

attaching the implant to tissue located near the mitral valve, wherein attaching the implant to the tissue includes (a) introducing a catheter into the left ventricle using the guide element as a track, wherein the catheter includes at least one pointed wire, the pointed wire including a tip section, the pointed wire further being configured to carry a coupling element, the tip section being configured for insertion into the implant and the tissue, (b) pushing the tip section through the implant and the tissue, wherein pushing the tip section through the implant and the tissue positions at least a part of the coupling element on an atrial side of the tissue, and (c) retracting the tip section from the implant and the tissue, wherein retracting the tip section causes the coupling element to substantially couple the implant with the tissue;

reducing an arc length of the implant, wherein reducing the arc length of the implant substantially reduces an arc length associated with the mitral valve; and removing the guide element from the left ventricle after attaching the implant to the tissue.

5. A method as recited in claim 4 wherein the coupling element is a T-bar.

6. A method as recited in claim 4 wherein the tissue is fibrous tissue.

7. A method for performing annuloplasty on a mitral valve of a heart, the method comprising:

inserting a first catheter assembly into a left ventricle through an aorta of the heart and an aortic valve of the heart;

positioning a guide element along a wall of the left ventricle beneath the mitral valve using the first catheter assembly, wherein the first catheter assembly includes a first catheter and a second catheter, the second catheter being located at least partially within the first catheter, the first catheter being arranged to facilitate the positioning of the second catheter along the wall of the left ventricle, and wherein positioning the guide element along the wall includes inserting the guide element through the second catheter, and anchoring the guide element against the wall;

positioning at least one implant in the left ventricle beneath the mitral valve using the guide element as a guide; and connecting the at least one implant to tissue near the mitral valve.

8. A method as recited in claim 7 further including:

removing the first catheter and the second catheter from the left ventricle; and inserting a third catheter into the left ventricle, the third catheter configured to carry the implant and to use the guide element as a guide.

9. A method for performing annuloplasty on a mitral valve of a heart, the method comprising:

inserting a first catheter assembly into a left ventricle through an aorta of the heart and an aortic valve of the heart;

positioning a guide element along a wall of the left ventricle beneath the mitral valve using the first catheter assembly;

positioning at least one implant in the left ventricle beneath the mitral valve using the guide element as a guide; and connecting the at least one implant to tissue near the mitral valve, wherein connecting the implant to the tissue near the mitral valve includes inserting a second catheter into the left ventricle, the second catheter being configured to carry a first connection element and inserting the first connection element through the implant and the tissue such that the implant and the tissue are coupled by the first connection element, wherein the second catheter is further configured to carry a second connection element; and inserting the second connection element through the implant and the tissue such that the implant and the tissue are coupled by the second connection element.

10. A method for performing annuloplasty on a mitral valve of a heart, the method comprising:

inserting a first catheter assembly into a left ventricle through an aorta of the heart and an aortic valve of the heart;

positioning a guide element along a wall of the left ventricle beneath the mitral valve using the first catheter assembly;

positioning at least one implant in the left ventricle beneath the mitral valve using the guide element as a guide, wherein positioning the implant in the left ventricle beneath the mitral valve using the guide element further includes inserting at least one balloon into the left ventricle and inflating the balloon, wherein inflating the balloon positions the implant generally against the mitral valve; and connecting the at least one implant to tissue near the mitral valve, wherein connecting the implant to the tissue near the mitral valve includes inserting a second catheter into the left ventricle, the second catheter being configured to carry a first connection element and inserting the first connection element through the implant and the tissue such that the implant and the tissue are coupled by the first connection element.

11. A method for performing annuloplasty on a mitral valve of a heart, the method comprising:

inserting a first catheter assembly into a left ventricle through an aorta of the heart and an aortic valve of the heart;

positioning a guide element along a wall of the left ventricle beneath the mitral valve using the first catheter assembly;

positioning at least one implant in the left ventricle beneath the mitral valve using the guide element as a guide, wherein positioning the implant in the left ventricle beneath the mitral valve using the guide element further includes inserting at least one expandable element into the left ventricle and expanding the expandable element, wherein expanding the expandable element positions the implant generally against the mitral valve; and connecting the at least one implant to tissue near the mitral valve, wherein connecting the implant to the tissue near the mitral valve includes inserting a second catheter into the left ventricle, the second catheter being configured to carry a first connection element and inserting the first connection element through the implant and the tissue such that the implant and the tissue are coupled by the first connection element.

* * * * *